(12) United States Patent
Walker et al.

(10) Patent No.: US 9,121,017 B2
(45) Date of Patent: Sep. 1, 2015

(54) DYNAMIC THERMORESPONSIVE NANOPARTICLES FOR STABILIZATION OF ENZYMES AT HIGH TEMPERATURES

(71) Applicants: Jeremy P. Walker, Oakmont, PA (US); Anna M. Leech, Pittsburgh, PA (US)

(72) Inventors: Jeremy P. Walker, Oakmont, PA (US); Anna M. Leech, Pittsburgh, PA (US)

(73) Assignee: FLIR Detection, Inc., Pittsburgh, PA (US)

( * ) Notice: Subject to any disclaimer, the term of this patent is extended or adjusted under 35 U.S.C. 154(b) by 79 days.

(21) Appl. No.: 13/888,771

(22) Filed: May 7, 2013

(65) Prior Publication Data

US 2013/0244301 A1 Sep. 19, 2013

Related U.S. Application Data

(62) Division of application No. 12/944,200, filed on Nov. 11, 2010, now Pat. No. 8,460,907.

(60) Provisional application No. 61/260,892, filed on Nov. 13, 2009.

(51) Int. Cl.
| | |
|---|---|
| *C12N 11/08* | (2006.01) |
| *A61K 31/74* | (2006.01) |
| *A61K 47/48* | (2006.01) |
| *C12N 9/96* | (2006.01) |

(52) U.S. Cl.
CPC ............... *C12N 11/08* (2013.01); *A61K 31/74* (2013.01); *A61K 47/48046* (2013.01); *A61K 47/48176* (2013.01); *C12N 9/96* (2013.01); *C12Y 101/03004* (2013.01); *C12Y 301/08001* (2013.01)

(58) Field of Classification Search
IPC .......... A61K 31/74,47/48046, 47/48176; C12N 11/08, 9/96; C12Y 101/03004, 301/08001
See application file for complete search history.

(56) References Cited

U.S. PATENT DOCUMENTS

| | | | |
|---|---|---|---|
| 5,310,786 | A | 5/1994 | Vorlop et al. |
| 6,291,200 | B1 | 9/2001 | LeJeune et al. |
| 6,673,565 | B2 | 1/2004 | LeJeune et al. |
| 6,759,220 | B1 | 7/2004 | LeJeune et al. |
| 6,762,213 | B2 | 7/2004 | LeJeune et al. |
| 2007/0248567 | A1 | 10/2007 | Pathak et al. |
| 2008/0138430 | A1 | 6/2008 | Owens et al. |

FOREIGN PATENT DOCUMENTS

| | | | | |
|---|---|---|---|---|
| WO | | 99/12975 | 3/1999 | |
| WO | | 02/34902 | 5/2002 | |
| WO | | 2008/004988 | 1/2008 | |
| WO | WO 2008004988 | A1 * | 1/2008 | ................ C08F 2/06 |

OTHER PUBLICATIONS

Hartree. 1968. A Comparison of Horseradish Peroxidase and Manganese Ions as Catalysts for the Oxidation of Dihydroxyfumaric Acid. Biochemical Journal, vol. 107, pp. 581-587; especially, p. 587, col. 1, Lines 12-31.*
Jaworek et al. 1976. Preparation and Properties of Enzymes Immobilized by Copolymerization. Methods in Enzymology, vol. 44, pp. 195-201.*
PCT Invitation to Pay Additional Fees and, where applicable, protest fee for PCT /US2010/056331 dated Jul. 1, 2011.
International Search Report and Written Opinion for PCT/US2010/ 056331 dated Mar. 22, 2011.
Retama et al., "Microstructural Modifications Induced by the Entrapped Glucose Oxidase in Cross-Linked Polyacrylamide Microels Used as Glucose Sensors", Biomaterials, 24, 2003, 2965-2973.
Tumturk, H., Preparation and application of poly(N,N-dimethylacrylamide-co-acrylamide) and poly(N-isopropylacryiamide-co-acrylamide)/K-Carrageenan Hydrogels for Immobilization of Lipase, International Journal of Biological Macromolecules, 2007, 281-285, vol. 40, Elsevier B.V.
Hamerska-Dudra, A., Immobilization of Glucoamylase and Trypsin on Crosslinked Thermosensitive Carriers, ScienceDirect, 2007, 197-204, vol. 41, Elsevier, Inc.
Chen, G., Preparation and Properties of Thermoreversible, Phase-Separating Enzyme-Oligo(N-isopropylacrylamide) Conjugates, Bioconjugate Chem., 1993, 509-514, vol. 4, American Cancer Society.
Ping Chen, J., Polymer-Protein Conjugates I. Effect of Protein Conjugation on the Cloud Point of poly(N-isopropylacrylamide), Biomaterials, 1990, 625-630, vol. 11, Butterworth-Heinemann Ltd.
Supplementary European Search Report and Search Opinion, May 21, 2013.

* cited by examiner

*Primary Examiner* — Debbie K Ware
*Assistant Examiner* — Kailash C Srivastava
(74) *Attorney, Agent, or Firm* — Buchanan Ingersoll & Rooney PC; Craig G. Cochenour

(57) ABSTRACT

The present invention provides a thermoresponsive nanoparticle useful for the stabilization of enzymes in environments having a temperature greater than thirty degrees Centigrade. The thermoresponsive nanoparticle has (a) a functionalized enzyme conjugate having one or more enzymes or biological catalysts, the enzymes or biological catalysts are modified with palmitic acid N-hydroxysuccinimide ester and acryclic acid N-hydroxysuccinimide ester, and (b) a thermally responsive polymer, wherein the functionalized enzyme conjugate is encapsulated within the thermally responsive polymer. A nanocatalyst is provided that has one or more proteins. The proteins are covalently immobilized and encapsulated within a thermally responsive polymer shell. The proteins are one or more enzymes or biological catalysts. A method for protecting the proteins is also set forth.

8 Claims, 20 Drawing Sheets

Diameter (size in nanometers) of Organophosphorus hydrolase encapsulated thermally-responsive nanoparticles as a function of temperature NiPAAm Hysteresis: Diameter changes as a function of temperature H -> L = High Temperature to Low Temperature Cycle
L -> H = Low Temperature to High Temperature Cycle Organophosphorus Hydrolase activity after thermal cycling (1 thermal cycle = temperature changes from 25º C to 60°C to 25°C)

Figure 6

Half life ($t_{1/2}$) of thermal inactivation (in hours) for Organophosphorus Hydrolase Samples

| Sample | 50°C T1 half (hours) | 60°C T1 half (hours) | 70°C T1 half (hours) |
|---|---|---|---|
| OPH | 2.5 | 1.5 | 1.5 |
| OPH + Nanoparticles | 3.5 | 1.5 | 1 |
| Functionalized OPH | 5.5 | 2 | 1.5 |
| Functionalized OPH + Nanoparticles | 6 | 2 | 2 |
| Encapsulated OPH | 24 | 10 | 4 |

Activity of organophosphorus hydrolase samples after incubation with sodium dodecylsulfate (SDS).

Diameter (size) in nanometers of OPH encapsulated into acrylamide nanoparticles and OPH encapsulated into NiPAAm nanoparticles as a function of temperature.

Figure 9B

Half life ($t_{1/2}$) of thermal inactivation (in hours) for Organophosphorus Hydrolase samples encapsulated into non-thermal responsive (acrylamide) nanoparticles and thermally-responsive (NiPAAm) nanoparticles.

|  | 50°C<br>T 1 half (hours) | 60°C<br>T 1 half (hours) | 70°C<br>T 1 half (hours) |
|---|---|---|---|
| OPH | 2.5 | 1.5 | 1.5 |
| OPH / Acrylamide | 8 | 4 | 2.5 |
| OPH / NiPAAm | 24 | 10 | 4 |

Activity of organophosphorus hydrolase encapsulated into non-thermal responsive (acrylamide) nanoparticles and thermally-responsive (NiPAAm) nanoparticles after incubation with sodium dodecylsulfate (SDS).

Diameter (size) in nanometers of Gluocse oxidase encapsulated thermally-responsive nanoparticles as a function of temperature

Figure 13

Half life ($t_{1/2}$) of thermal inactivation (in hours) for Glucose oxidase samples

| Sample | 50°C<br>T 1 half<br>(hours) | 60°C<br>T1 half<br>(hours) | 70°C<br>T1 half<br>(hours) |
|---|---|---|---|
| GOx | 2 | <0.5 | <0.25 |
| GOx + Nanoparticles | 2.5 | <0.5 | <0.25 |
| Functionalized GOx | 3.5 | 1 | <0.5 |
| Functionalized GOx + Nanoparticles | 3.5 | 1 | <0.5 |
| Encapsulated GOx | 16 | 7.5 | 0.5 |

Shelf life (dry storage) of native and encapsulated Glucose oxidase at 70°C.

Figure 16

Diameter (size) in nanometers of Acetylcholinesterase encapsulated thermally-responsive nanoparticles as a function of temperature Aqueous stability / pot life of acetylcholinesterase samples at 40°C.

Aqueous stability / pot life of acetylcholinesterase samples at 50°C.

DYNAMIC THERMORESPONSIVE NANOPARTICLES FOR STABILIZATION OF ENZYMES AT HIGH TEMPERATURES

CROSS REFERENCE TO RELATED APPLICATION

The present utility patent application is a divisional patent application of and claims the benefit of priority to U.S. patent application Ser. No. 12/944,200, filed Nov. 11, 2010, now U.S. Pat. No. 8,460,907 B2 granted Jun. 11, 2013, which claims the benefit of priority to U.S. Provisional Patent Application Ser. No. 61/260,892, filed Nov. 13, 2009, now expired. The entire contents of U.S. patent application Ser. No. 12/944,200 and U.S. Provisional Patent Application Ser. No. 61/260,892 are incorporated by reference into this utility patent application.

GOVERNMENT INTEREST

Certain embodiments of this invention were made with Government support under Contract No. HDTRA1-08-1-0054 awarded by United States of America, Department of Defense. The Government has certain rights in the invention.

FIELD OF THE INVENTION

The present invention relates to a material and a method of encapsulating and covalently immobilizing enzymes within thermally responsive nanoparticles. Three-dimensional immobilization of enzymes within nanoparticles that selectively respond to thermal stimuli (thermo-responsive nanoparticles) provides a methodology for protecting enzymes from elevated temperature conditions which might otherwise destroy the enzymes. Native enzymes unfold at elevated temperatures and rapidly lose their catalytic activity. The present invention provides enzymes that are functionalized with hydrophobic and polymerizable chemical groups, allowing the enzymes to participate as a comonomer in the enzyme-friendly nanoparticle synthesis reaction. The resulting covalent immobilization of the enzyme with the nanoparticle allows the tertiary structure of the enzyme to stay intact due to contraction of the nanoparticle at elevated temperatures. Thus, enzyme stability in both the aqueous state and dry state is greatly enhanced at elevated temperatures (>30° C.).

BACKGROUND OF THE INVENTION

Enzymes are biological proteins that speed up chemical reactions by lowering the energy barrier for them to occur more easily. Enzymes demonstrate a high degree of utility due to their speed of reaction, specificity for certain analytes, and ability to be engineered and chemically modified. Enzymes are used in many industries including food processing, detergents and cleaning products, clinical diagnostics, fuel production and decontamination of chemical agents. The major problem associated with the practical utility of enzymes is the inability to sufficiently stabilize their tertiary structure in harsh environmental conditions, such as high temperatures, extreme pH, high salinity and solvents; free enzymes are susceptible to damage and will incur partial or total activity loss in the presence of such conditions. As a result, applications of free enzymes for large scale commercial use, especially for continuous use, are extremely limited. The ability to stabilize enzymes in harsh conditions is an area of immense interest; retention of activity in non optimized environments, such as elevated temperatures, will improve catalytic performance and be beneficial for countless applications.

Various approaches for stabilizing enzymes have been demonstrated from enzyme adsorption and modification to recombinant protein engineering; these methods only provide a moderate improvement in enzyme stability. Stability of enzymes adsorbed onto nanoparticles is highly dependant on nanoparticle size and adsorption pattern. Protein and nanoparticle interactions during adsorption can cause conformational changes to an enzyme's native structure, rendering it inactive. Entrapment of enzymes has been demonstrated to improve the stability by restricting their ability to unfold. Entrapment of oxidase enzymes within inorganic silica nanogels were shown to improve the stability over the native form by up to 200-fold. To date, the optimal method for enhancing the stability of enzymes has been three-dimensional covalent immobilization of enzymes. LeJeune and Russell demonstrated that hydrolase enzymes which detoxify chemical warfare agents could be immobilized within polyurethane foams. The surface lysine residues participate in the crosslinking reaction by condensing with the isocyanate groups on the polyurethane backbone, resulting in a foam material that contains active enzymes which retain superior stability over the native enzyme [see, LeJeune, K. E., "Covalent binding of a nerve agent hydrolyzing enzyme within polyurethane foams", Biotechnology and Bioengineering, Vol. 51, pages 450-457 (1996), and LeJeune, K. E., "Dramatically stabilized phosphotriesterase-polymers for nerve agent degradation", Biotechnology and Bioengineering, Vol. 54, pages 105-114 (1997)]. This work has been extended to numerous enzymes which have been utilized to make colorimetric sensor pens that have shelf-lives of years and can withstand harsh environmental conditions such as heat and solvents (see also U.S. Pat. Nos. 6,291,200; 6,673,565; 6,762,213; and 6,759,220).

Recently, there has been a large focus on nanoparticle development in many fields including: optics and coatings, clinical diagnostics, drug-delivery, and also in the development of novel materials such as self-healing and highly-porous plastics. Stabilization of covalently-immobilized enzymes within porous, hydrophilic nanogels has been demonstrated by several groups. Polymers which respond to specific stimuli, such as temperature and the presence of other molecules in solution are frequently utilized in particle development. Nanoparticles composed of such polymers have the capability to shrink and swell via changes in Gibbs free energy in the presence of the proper stimulus. Responsive nanoparticles are currently used for drug delivery, bioimaging and therapeutics. The present invention provides three-dimensional immobilization of enzymes at the nanoscale within thermally responsive polymer materials which will protect the enzyme by providing a responsive barrier material that will respond to environmental stimuli to provide structural support under conditions that would otherwise denature the enzyme.

Enzymes have been functionalized and coupled with N-isopropylacrylamide (NiPAAm) with N-hydroxysuccinimide (NHS) [Chen, G., "Preparation and properties of thermoreversible, phase-separating enzymes-oligo (N-isopropylacrylamide) conjugates", Bioconjugate Chemistry, Vol. 4, pages 509-514 (1993)]. NiPAAm is a thermo-responsive polymer that which undergoes a volume transition at temperatures above its lower critical solution temperature (LCST) approximately 32° C. Coupling NiPAAm to an enzyme allows it to be used for separation, recovery, and recycling of an enzyme simply by applying small temperature changes to the reaction medium. The growing NiPAAm enzyme chains have also shown moderate improvements in stability compared to native enzyme. However, heretofore, no one has cross-linked an enzyme or encapsulating an enzyme within thermally responsive (thermoresponsive) nanoparticles, as set forth in the present invention.

Incorporation of functional enzymes into nanoparticles is difficult for several reasons. Bottle-in approaches have limited utility because diffusion of enzymes into polymer particles, on a short time scale, is difficult due to small pore size and high polymer concentration on the outer particle shell. Harsh conditions during nanoparticle fabrication such as solvents, surfactants and high temperatures can be detrimental to the tertiary structure of the enzyme. The present invention provides an enzyme-friendly methodology for covalently immobilizing and encapsulating enzymes within stimulus responsive nanoparticles using standard oil-in-water emulsion polymerization protocols, such emulsion polymerization protocols are known by those persons skilled in the art. Essentially, hydrophobic graft-modified enzymes can be used as seeds in micelle systems for growth of nanoparticles. Incorporating functional enzymes into nanoparticles which are constructed from responsive polymers will further stabilize enzymes in harsh environments (for example, elevated temperature, chemicals, unfavorable pH, physical forces—all stressful).

Enzymes modified with NiPAAm polymers have shown an increased thermal stability over native enzymes. Through encapsulating and immobilizing an enzyme within responsive NiPAAm nanoparticles, the stability will be greatly improved at elevated temperatures; leading to a drastic improvement in both pot life (aqueous state) and shelf life (dry state) stability. The contraction of the particles supports the enzyme's tertiary structure, leaving the enzyme highly folded and active at elevated temperatures; free enzymes which are unencapsulated will unfold at these temperatures and become inactive.

The resulting functionalized enzyme conjugate-nanoparticle systems of the present invention have numerous applications. Enzymes generally demonstrate immense utility for a variety of industrial catalysis reactions; however the byproducts or intense environmental conditions limit the efficiency of using enzymes. The nanocatalysts and nanoparticles of the present invention stabilize enzymes to survive such intense environmental conditions including, such as for example but not limited to, temperature extremes. The nanocatalysts and nanoparticles of the present invention have high degree of utility for decontamination, chemical remediation, drug delivery, wound healing, protein therapy and a host of other applications.

SUMMARY OF THE INVENTION

This invention provides a dynamic thermally responsive (thermoresponsive) nanoparticle(s) for stabilization of enzymes and other proteins at elevated temperatures.

Another embodiment of the present invention provides a nanocatalyst comprising one or more proteins, the proteins are covalently immobilized and encapsulated within a thermally responsive polymer shell. The immobilized and encapsulated protein of the nanocatalyst, as described herein, is one or more enzymes or biological catalysts. The nanocatalyst includes wherein the covalently immobilized and entrapped enzyme or biological catalyst remains in a folded position and retains its active conformation.

In another embodiment of the nanocatalyst of the present invention, the nanocatalyst includes wherein at least one of the proteins are covalently immobilized via at least one of the moieties selected from the group consisting of amines, carboxylates or thiols pendant from the protein or via at least one carbohydrate group attached to the protein. The nanocatalyst preferably includes wherein the encapsulated enzyme retains activity ranging from 5 to 100% of the enzyme's native catalytic activity. Another embodiment of the present invention includes the nanocatalyst, as described herein, wherein the polymer shell comprises one or more fully or partially thermally responsive polymers. The thermally responsive polymer is a polymer selected from the group consisting of a poly(N-isopropylacrylamide), a poly(isopropyl-N-vinylpyrrolidone), a polymer which undergoes a conformational change when heated, and combinations thereof.

Another embodiment of this invention provides a method for protecting proteins from environmental conditions comprising immobilizing one or more proteins and encapsulating the one or more immobilized proteins within one or more polymeric nanoparticles for protecting the protein from detrimental environmental conditions. The method includes covalently grafting at least one moiety to the enzyme for enabling the enzyme to covalently bind to the polymer. This moiety may be, for example, but not limited to, a vinyl group. Further, this method includes subjecting the graft-modified enzyme to a polymerization process. The polymerization process is, for example but not limited to, a free-radical addition polymerization process or a living radical polymerization process. The free-radical polymerization process is selected from the group consisting of an emulsion polymerization process and a non-emulsion polymerization process, all of which are known by those skilled in the art. The method, as described herein, provides that the free-radical polymerization process optionally includes at least one thermally responsive comonomer selected from the group consisting of a N-isopropylacrylamide, poly(isopropyl-N-vinylpyrrolidone), a polymer which undergoes a conformational change when heated, and combinations thereof.

Another embodiment of the present invention provides a nanoparticle comprising a functionalized enzyme conjugate comprising one or more enzymes or biological catalysts, and wherein the enzymes or biological catalysts of the functionalized enzyme conjugate are modified with palmitic acid N-hydroxysuccinimide ester and acrylic acid N-hydroxysuccinimide ester; and a thermally responsive polymer, and wherein the functionalized enzyme conjugate is encapsulated within the thermally responsive polymer. The nanoparticle, as described herein, includes wherein the thermally responsive polymer is one or more selected from the group consisting of a N-isopropylacrylamide, and a N-isopropylacrylamide and polystyrene polymer. Another embodiment of this invention includes wherein the nanoparticle, as described herein, further includes a cross-linking agent and an initiator agent for encapsulating the functionalized enzyme conjugate within the thermoresponsive polymer.

It will be appreciated by those persons skilled in the art that the present invention provides a material and a method of encapsulating and covalently immobilizing enzymes within thermally responsive nanoparticles. Immobilization of enzymes within nanoparticles that selectively respond to elevated temperatures (temperatures above 30 degrees Centigrade) otherwise known as thermally responsive nanoparticles, provides a methodology for protecting enzymes from harsh environmental conditions which might otherwise destroy the enzymes.

This invention combines the advantages of enzymatic catalysis with the benefits afforded by operating on the nano scale (large surface area-to-volume, fast diffusion, fast conformational changes, and other properties known by those skilled in the art) to result in responsive nanoparticles containing enzymatic catalysts that can be protected from elevated temperatures. The ability to maintain or enhance the stability of enzymes at high temperatures has significant application in the fields of industrial catalysis, decontamination, and field-portable diagnostics.

BRIEF DESCRIPTION OF THE DRAWINGS

FIG. 6 shows the half-life ($t_{1/2}$) of thermal inactivation for enzyme encapsulated nanoparticles. The half-life of thermal inactivation is noted in hours in the figure. The aqueous stability (pot life) of organophosphorus hydrolase (OPH), OPH+nanoparticles, functionalzied OPH, functionalized OPH+nanoparticles and OPH encapsulated nanoparticles at elevated temperatures. OPH pot life is enhanced through encapsulation in thermoresponsive nanoparticles by: 10-fold at 50° C., 6.67-fold at 60° C. and 2.67-fold at 70° C.

FIG. 9B shows organophosphorus hydrolase (OPH) encapsulated into NiPAAm or acrylamide nanoparticles and the resulting half life of thermal inactivation for OPH. Aqueous solutions of native OPH and encapsulated OPH were stored at elevated temperatures and aliquots were periodically removed and assayed for catalytic activity. The half life of thermal inactivation is noted in hours; contraction of the NiPAAm nanoparticles provides steric support and prevents enzyme denaturation at elevated temperatures. Catalytic activity is greatly enhanced by encapsulation within thermo-responsive nanoparticles. Pot life/aqueous stability is increased through encapsulation in thermally responsive nanoparticles.

2,2'-azino-bis(3-ethylbenzthiazoline-6-sulphonic acid) ("ABTS") is a chemical compound used to observe the reaction kinetics of specific enzymes. FIG. 11 shows ABTS as a substrate with hydrogen peroxide ($H_2O_2$). ABTS allows the reaction kinetics of peroxidases (horseradish peroxidase) to be followed and indirectly follows the reaction kinetics of any hydrogen peroxide-producing enzyme or to simply quantify the amount of hydrogen peroxide in a sample.

FIG. 13 shows the half-life ($t_{1/2}$) of thermal inactivation for aqueous stability (pot life) of glucose oxidase (GOx) encapsulated nanoparticles. The half-life of thermal inactivation is noted in hours. GOx, GOx+nanoparticles, functionalized GOx, functionalized GOx+nanoparticles and GOx encapsulated nanoparticles at elevated temperatures. GOx pot life is enhanced through encapsulation in thermoresponsive nanoparticles by: 8-fold at 50° C., 15-fold at 60° C. and 2-fold at 70° C.

FIG. 16 shows acetylcholinesterase (AChE) encapsulated thermoresponsive nanoparticles and their size response to temperature. At ambient temperatures the nanoparticles are 325 nm in diameter and shrink to 225 nm in diameter at elevated temperatures.

FIG. 17A shows AChE pot life at 40° C. is increased by 6.5 fold and FIG. 17B shows AChE pot life is increased by 3 fold at 50° C. for the functionalized AChE conjugate thermally responsive nanoparticles of the present invention.

DETAILED DESCRIPTION OF THE INVENTION

Figure 1:
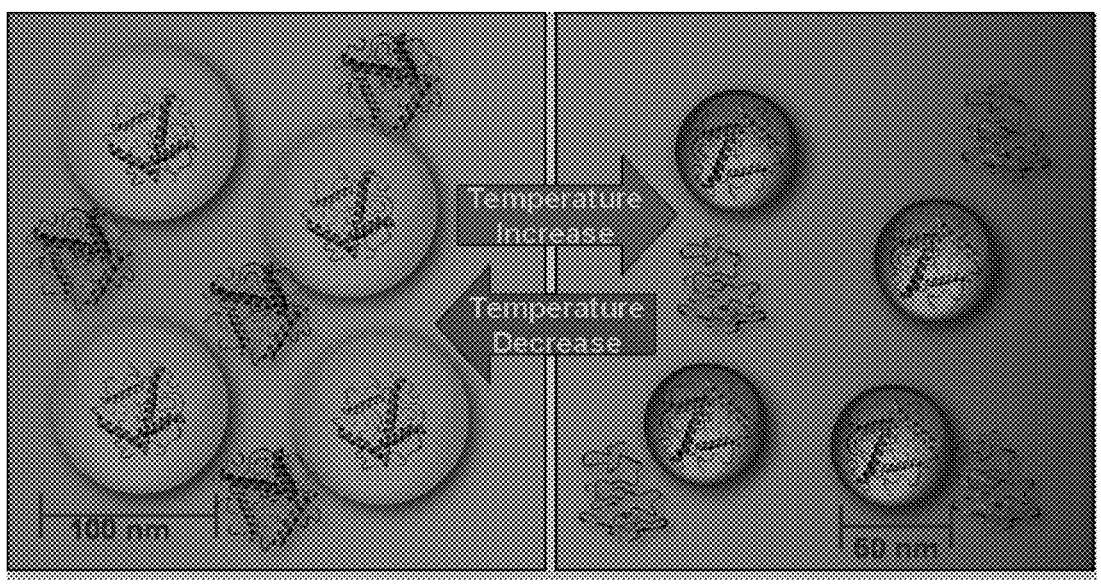
FIG. 1 shows a representation of the affect temperature has on free enzymes and encapsulated enzyme within thermally responsive nanoparticles. Free enzymes denature when exposed to increases in temperature, while encapsulated enzyme's tertiary structure is protected by the collapsing particle.

This invention provides a dynamic thermally responsive (thermoresponsive) nanoparticle(s) for stabilization of enzymes and other proteins at high temperatures. The terms "high temperature" and "high temperatures", as used herein, are defined as temperatures that are greater than 30 degrees Centigrade, and more preferably temperatures ranging from greater than 30 degrees Centigrade up to 100 degrees Centigrade. The term "low temperature" and "low temperatures", as used herein, are defined as temperatures ranging from 30 degrees Centigrade and below, and more preferably temperatures ranging from 30 degrees Centigrade to zero (0) degrees Centigrade.

The term "enzyme" and enzymes", as used herein, refers generally to proteins that catalyze biochemical reactions. Enzymes are proteins that generally enable chemical transformations of organic compounds. Enzymes are powerful catalysts because they are highly specific. The thermally responsive nanoparticles of the present invention stabilize enzymes and biological catalysts. Preferably the enzymes are selected from the group consisting of lyases, hydrolases, oxidoreductases, transferases, isomerases, and ligases, and combinations thereof. In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC2 (Enzyme Class 2) Transferases. Enzymes catalyzing hydrolysis are referred to generally as EC 3 Hydrolases. Enzymes catalyzing removal from or addition to a substrate of specific chemical groups are referred to generally as EC 4 Lyases. Enzymes catalyzing isomerization are referred to generally as EC 5 Isomerases. Enzymes catalyzing combination or binding together of substrate units are referred to generally as EC 6 Ligases. Hydrolase enzymes include, but are not limited to, a lipase, a phosphatase, an amylase, a cellulase, a protease, a peptidase, a urease, or a deaminase. Specific examples of suitable hydrolases include but are not limited to, organophosphorus hydrolase (OPH), organophosphorus acid anhydrolase (OPAA), urease, butyrylcholinesterase or acetylcholinesterase. One or a plurality of enzymes, or combinations thereof, may be incorporated within the thermally responsive nanoparticles of the present invention. In a most preferred embodiment of the thermally responsive nanoparticles of the present invention as described herein, one or more purified enzymes are selected from the group consisting of one or more of organophosphorus acid anhydrolase (OPAA), organophosphorus hydrolase (OPH), glucose oxidase (GOx), and acetylcholinesterase (AChE).

The term "biological catalyst" and "biological catalysts", as used herein, refer to a substance that increases the rate of biological processes or reactions, and is for example, an enzyme. An enzyme is a protein that functions as a biological catalyst. Enzymes catalyse reactions by lowering the activation energy—the energy input needed to bring about the reaction.

The term "denatured enzyme", as used herein, refers to an enzyme that can not operate because the shape of its active site is altered thus the substrate can not combine with it—change in shape resulting in loss of biological function.

The present invention provides a nanocatalyst comprising one or more proteins, the proteins are covalently immobilized and encapsulated within a thermally responsive polymer shell. The polymer shell preferably has a diameter between 5 nanometers and 500 nanometers. The immobilized and encapsulated protein of the nanocatalyst, as described herein, is one or more enzymes or biological catalysts. The nanocatalyst includes wherein the covalently immobilized and entrapped enzyme or biological catalyst remains in a folded position and retains its active conformation.

The terms "protein" and "proteins", as used herein, refers to any of a group of complex organic macromolecules that contain carbon, hydrogen, oxygen, nitrogen, and usually sulfur, and include such as for example but not limited top, substances such as enzymes, hormones, and antibodies. "Proteins" include addition enzymes such as asparaginase and non-catalytic proteins such as erythropoietin. "Proteins" may be of many types, such as for example but not limited to, the following:

Hormones are proteins that are responsible for the regulation of many processes in organisms. Hormones are usually quite small and can be classifies as peptides. Most known protein hormones are: insulin, grows factor, lipotropin and prolactin. Many protein hormones are predecessor of peptide hormones, such as endorfine and enkephalin.

Transport proteins are proteins that transport (or store) other chemical compounds and ions, such as: cytochrome C, an electron transport protein, haemoglobin and myoglobin oxygen transport proteins and albumin, a fatty acid transport protein in the blood stream.

Antibodies are proteins that are involved in the immune response. Sometimes antibodies can act as enzymes. Antibodies can also be classified into a larger groups of proteins called protective proteins, such as: lymphocyte antigen-recognizing receptors, antivirals agents such as interferon and tumor necrosis factor. Fibrin and thrombin (blood clotting proteins) should be classified as protective proteins as well.

Structural proteins are proteins that maintain structures of other biological components, like cells and tissues. Collagen, elastin, α-keratin, sklerotin and fibroin are proteins that are involved in the formation of the whole organism body. Bacterial proteoglycans and virus coating proteins also belongs to this group of proteins.

Motor proteins are proteins that can convert chemical energy into mechanical energy, such as, actin and myosin which are responsible for muscular motion.

Receptors are proteins that are responsible for signal detection and translation into other type of signal. Sometimes these proteins are active only in complex with low molecular weight compounds. Rhodopsin, a light detecting proteins is a well known member of this protein family.

Signalling proteins are proteins that are involved in signaling translation processes. Typically they change conformation significantly in the presence of a signaling molecule. These proteins can sometimes act as enzymes.

Storage proteins are proteins that contain energy, which can be released during metabolism processes in an organism. Egg ovalbumin and milk casein are examples of such storage proteins.

Enzyme Factor VIIa is a coagulation protein that may be used for uncontrollable bleeding, such as in patients affected with hemophilia or uncontrolled hemorrhage. Each of the herein described examples of proteins may be encapsulated into the thermally responsive nanoparticles of the present invention.

In another embodiment of the nanocatalyst of the present invention, the nanocatalyst includes wherein at least one of the proteins are covalently immobilized via at least one of the moieties selected from the group consisting of amines, carboxylates or thiols pendant from the protein or via at least one carbohydrate group attached to the protein. The nanocatalyst preferably includes wherein the encapsulated enzyme retains activity ranging from 5 to 100% of the enzyme's native catalytic activity.

The polymer shell of the nanocatalyst of the present invention, as described herein, comprises one or more thermoresponsive polymers which undergo a transition from having a hydrophilic character to having a hydrophobic character above a specific lower critical solution temperature. The thermally responsive polymer shell is collapsible as the environmental temperature rises and the enzyme of the functionalized enzyme conjugate (seed) remains highly folded and in an undenatured state (i.e native state). The term "highly folded', as used herein, is a term of art known by those persons skilled in the art and refers to the conformation of proteins (for example in the native state) having a plurality of folds in their structure.

Another embodiment of the present invention includes a nanocatalyst, as described herein, wherein the polymer shell comprises one or more fully or partially thermally responsive polymers. The thermally responsive polymer is a polymer selected from the group consisting of a poly(N-isopropylacrylamide), a poly(isopropyl-N-vinylpyrrolidone), a polymer which undergoes a conformational change when heated, and combinations thereof.

It will be appreciated by those persons skilled in the art that the nanocatalyst of the present invention provides for an encapsulated protein that has improved stability over a native protein at temperatures greater than 30 degrees Centigrade in both aqueous solutions and dry powders. The nanocatalyst of the present invention has a covalently immobilized protein that is stable at temperatures below 30 degrees Centigrade and is stable ranging from zero (0) degrees Centigrade to 30 degrees Centigrade. Further, the nanocatalyst of the present invention having an encapsulated protein is stable at temperatures greater than 30 degrees Centigrade.

Another embodiment of this invention provides a method for protecting proteins from environmental conditions comprising immobilizing one or more proteins and encapsulating the one or more immobilized proteins within one or more polymeric nanoparticles for protecting the protein from detrimental environmental conditions. The method, as described herein, including wherein the protein is at least one enzyme or at least one biological catalyst. The method provides including covalently grafting at least one moiety to the enzyme for enabling the enzyme to covalently bind to the polymer. This moiety may be, such for example but not limited to, a vinyl group.

The method, as described herein, includes subjecting the graft-modified enzyme to a polymerization process. The polymerization process is, for example but not limited to, a free-radical addition polymerization process or a living radical polymerization process. The free-radical polymerization process is selected from the group consisting of an emulsion polymerization process and a non-emulsion polymerization process, all of which are known by those skilled in the art. The method, as described herein, including wherein the free-radical polymerization process optionally includes at least one thermally responsive comonomer selected from the group consisting of a N-isopropylacrylamide, poly(isopropyl-N-vinylpyrrolidone), a polymer which undergoes a conformational change when heated, and combinations thereof.

Another embodiment of the present invention provides a nanoparticle comprising a functionalized enzyme conjugate comprising one or more enzymes or biological catalysts, the enzymes or biological catalysts of the functionalized enzyme conjugate are modified with palmitic acid N-hydroxysuccinimide ester and acrylic acid N-hydroxysuccinimide ester; and a thermally responsive polymer, the functionalized enzyme conjugate encapsulated within the thermally responsive polymer. The nanoparticle, as described herein, includes wherein the thermally responsive polymer is one or more selected from the group consisting of a N-isopropylacrylamide, and a N-isopropylacrylamide and polystyrene polymer. Preferably the enzymes are selected from the group consisting of lyases, hydrolases, oxidoreductases, transferases, isomerases, and ligases, and combinations thereof. More preferably, the enzymes are selected from the group consisting of a lipase, a phosphatase, an amylase, a cellulase, a protease, a peptidase, a urease, and a deaminase, and combinations thereof. Most preferably, the enzymes are selected from the group consisting of organophosphorus hydrolase (OPH), organophosphorus acid anhydrolase (OPAA), butyrylcholinesterase, glucose oxidase (GOx), acetylcholinesterase (AChE), dehalogenase (DHG), diisopropylfluorophosphatase (DFPase), and Factor VIIa. It will be appreciated by those skilled in the art that the nanoparticle of the present invention provides wherein the enzymes are incapable of unfolding under stressful environmental conditions, such as for example but not limited to, a temperature greater than 30 degrees Centigrade. Another embodiment of this invention includes wherein the nanoparticle, as described herein, further includes a cross-linking agent and an initiator agent for encapsulating the functionalized enzyme conjugate within the thermoresponsive polymer.

The application of enzymes is limited due to their poor stability in the presence of elevated temperatures. Known encapsulation techniques to date have focused on providing shells that essentially prevent/limit diffusion or prevent uptake of water. Silica encapsulation has worked well for shelf-life stability; however this technique alone is insufficient for providing operational stability to enzymes. Static shells are unable to dynamically change volume or porosity to limit diffusion and provide a support network for the enzyme. In contrast, the present invention describes a 2-step modification method that has been developed for functionalizing enzymes with vinyl moieties and hydrophobic groups that enable the functionalized enzymes to be encapsulated under a variety of different conditions, as set forth herein. Enzymes such as, but not limited to, organophosphorus hydrolase (OPH), glucose oxidase (GOx) and acetylcholinesterase (AChE) were modified with polymerizable and hydrophobic chemical groups. Functionalization of enzymes achieves two goals: it increases surface hydrophobicity which enables the enzyme to enter the interior of the aqueous micelle prior to nanoparticle synthesis, and provides vinyl functionality that can be used to covalently anchor the enzyme 3-dimensionally within the growing polymer via free-radical polymerization. The covalent attachments result in enhanced stability of the enzymes at elevated temperatures. After the enzyme is modified to produce a functionalized enzyme conjugate (seed), the method of the present invention further comprises employing an enzyme-friendly nanoparticle fabrication to produce the thermally responsive nanoparticles of the present invention.

In the method of the present invention, functionalized enzyme conjugates (seeds) are dispersed in a solution which may or may not contain a surfactant, at ambient or slightly above ambient temperatures. Comonomers, styrene and N-isopropylacrylamide (NiPAAm) were added to the reaction with a cross linker, N,N'-Methylenebisacrylamide. NiPAAm is a thermo-responsive polymer which undergoes a volume transition at temperatures above its lower critical solution temperature (LCST) approximately 32° C. After the monomer mixture was equilibrated, a water soluble initiator (initiation agent), potassium persulfate, was added to initiate the polymerization. At this time, the temperature was increased from 25° C. to 40° C.; the increase in temperature took approximately 10 minutes. Growing NiPAAm chains undergo a transition from being highly hydrophilic and swollen (at <32° C.) to shrunken and hydrophobic (at temperatures above the LCST). As the reaction temperature is raised to 40° C., the NiPAAm becomes hydrophobic and the grafting reaction occurs. To ensure the retention of catalytic activity throughout the polymerization process the reaction was then removed from the heat and placed in an ice bath. To continue the polymerization reaction while incubated on ice, a catalyst, tetramethylethylene was added. The synthesis reaction was allowed to proceed for 1 hour and the samples were then purified by centrifugation and dialysis to remove unreacted monomer.

The results of these processes are typically nanoparticles having a diameter in the size regime of 50-300 nm with low polydispersity. Thus, this invention provides thermally-responsive nanoparticles that contain covalently immobilized enzyme that remains active. The resulting encapsulated enzymes display an increase in both pot life and shelf life stability at elevated temperatures (greater than 30 degrees Centigrade).

Thermal stability studies in aqueous conditions were conducted at temperatures up to 70° C. Catalytic activity of encapsulated enzyme is higher relative to that of native or functionalized enzyme at elevated temperatures, typically resulting in a 2-15 fold improvement in enzyme pot-life. Lyophilization of these novel materials extends their shelf life (dry storage conditions) over that of native enzyme. After 3 weeks of dry storage at 70° C., native enzyme loses all activity; whereas encapsulated enzyme retains approximately 40% activity after 25 weeks at 70° C. Encapsulation of enzymes extends shelf life from 3 weeks to over 6 months.

Enzymes encapsulated into non-responsive particles were additionally created; showing no response to changes in temperature. These particles were thoroughly studied, alongside native enzyme and enzymes encapsulated into thermally-responsive nanoparticles for elevated aqueous stability at temperatures up to 70° C. While enzymes encapsulated into non-responsive particles increase pot life over native enzymes at elevated temperatures, the increase in stability is only moderate when compared to the increased stability obtained by encapsulation within thermally-responsive nanoparticles.

Additional studies have been performed using denaturants to illustrate that the enzyme is indeed immobilized within the nanoparticle. Unencapsulated enzymes and enzymes adsorbed unto a nanoparticle surface rapidly lost activity in the presence of a detergent, whereas enzymes encapsulated into the thermally responsive nanoparticles of the present invention slowly decreased enzymatic activity over a longer time course, indicating the enzymes are 3-dimensionally covalently immobilized within the nanoparticles.

The present invention provides functionalized enzyme conjugates that have enzymes that retain catalytic activity within NiPAAm nanoparticles. The enzyme is structurally supported via covalent immobilization and is further structurally supported at elevated temperatures by the collapsing NiPAAm network. The ability to maintain or enhance the stability of enzymes at high temperatures has significant application in the fields of industrial catalysis, decontamination, and field-portable diagnostics. FIG. 1 is a representation of an enzyme encapsulated within thermo-responsive N-isopropylacrylamide (NiPAAm)/Polystyrene particles. NiPAAm undergoes a volume transition at temperatures above its lower critical solution temperature (LCST) approximately 32° C. At temperatures <32° C. nanoparticles composed of NiPAAm are hydrophilic and highly swollen, their refractive index is similar to water and solutions containing these particles appear clear. Once heated above 32° C. the particles become more hydrophobic and shrink in size, collapsing upon themselves and increasing their refractive index, causing the solution to appear turbid. Given the ability to rapidly heat the solution, the response time is nearly instantaneous.

Temperature responsive polymers or otherwise known as thermally responsive polymers undergo a phase transition behavior at temperatures above and below a specific value known as the lower critical solution temperature (LCST). At temperatures above the LCST, the hydrophobic bonds within and between the molecules strengthen and the polymer chains aggregate (the polymer becomes more hydrophobic). Conversely, at temperatures lower than the LCST, the polymer chains bind to water molecules and become hydrated (the polymer is hydrophillic). This phase transition phenomenon is reversible. Thermally responsive polymers, as used herein, include such as for example, but not limited to, N-isopropylacrylamide (NiPAAm) and poly(N-isopropylacrylamide), and are the most studied thermally responsive (thermo-responsive) polymers and are utilized in this invention to fabricate the thermally responsive nanoparticles of the present invention. Additionally, it will be appreciated by those skilled in the art, that other thermally responsive polymers can be employed in the methods and nanoparticles of the present invention, such as but not limited to: N-acryloypyrrolidine, N-acryloyl piperidine, N-vinylisobutyramide, MA-PIPA, methylenebisacrylamide, N-isopropylmethacrylamide, and N-diethylacrylamide, to name a few, as well as polymers synthesized to exhibit thermoresponsive behavior, such as for example but not limited to, N-substituted poly[(meth)acrylamide]s, poly(N-vinylamide)s, poly(oxazoline)s, protein-related polymers, poly(ether)s, polymers based on amphilphilic balance and elastin-like synthetic polymers. Additionally, thermoresponsive polymers based on alkyl modified polyvinylpyrrolidone (PVP) can be employed in the present invention to produce thermo-responsive nanoparticle, such as for example but not limited to, poly-3-ethyl-1-vinyl-2-pyrrolidone (C2-PVP) and poly-3-butyl-1-vinyl-2-pyrrolidone (C4-PVP). These polymers exhibit very sensitive reversible temperature-dependant water solubility and the LCST can be tuned by modification of the alkyl group.

With regard to the cross linking agents employed in the method of the present invention, chemical covalent cross-links are stable mechanically and thermally, so once formed are difficult to break N'N-methylenebisacrylamide was used in the present invention as a cross linking agent (cross linker). Additional cross linkers, such as those commonly utilized in gel electrophoresis, can be substituted into the method for enzyme-friendly nanoparticle fabrication such as for example but not limited to, 1,4-Bis(acryloyl)piperazine, N,N'-Bis(acryloyl)cystamine, used as a reversible cross-linker for polyacrylamide gels—the disulfide linkage can be broken with a suitable reducing agent, polyethylene glycol diacrylate, N,N'-diallyltartardiamide, and bisacrylyl piperazine as well as additional crosslinkers but not limited to 2-Isocyanatoethyl methacrylate a crosslinker typically utilized for resins or coatings.

With regard to comonomers employed concerning the thermally responsive polymer, styrene is a comonomer used in the present invention to enhance the hydrophobic interaction of the thermo-responsive polymer—basically making the nanoparticles "like" to shrink more. Addition monomers can be substituted for styrene in the method for the enzyme-friendly nanoparticle synthesis of the present invention such as for example but not limited to, Butyl methacrylate, 1,3-Butadiene, Poly(styrene-co-4-vinylpyridine), Benzocyclobutene, poly(butyl acrylate-styrene).

With regard to the hydrophobic chemical group of the present invention, palmitic acid N-hydroxysuccinimide ester (paNHS) is employed in several of the examples herein. Palmitic acid N-hydroxysuccinimide ester can be substituted with any N-hydroxysuccinimide (NHS) ester that contains a vinyl group. It will be appreciated by those persons skilled in the art that the hydrophobic chemical group may be any acid that contains a vinyl group and ester (such as but not limited to 10-Undecenoic acid) but no NHS group can be coupled with 1-Ethyl-3-[3-dimethylaminopropyl]carbodiimide (EDC), a water soluble carbodiimide for rapid preparation of peptide conjugates that makes a 1-step amide crosslink between carboxylates and amines. Once the acid has been coupled with EDC it can be used in the first step of the modification procedure to modify the enzyme or protein of choice.

With regard to the polymerizable chemical group of the present invention, acrylic acid N-hydroxysuccinimide (aaNHS) is employed in several of the examples herein. It will be appreciated by those persons skilled in the art that any vinyl ester NHS can be substituted for acrylic acid NHS. Further, any vinyl ester that has been coupled with EDC can be used as the $2^{nd}$ modifier in the present inventions 2-step modification process of the present invention as described herein.

With regard to the initiators of the polymerization reaction, an initiator is used in the present invention to assist in the polymerization process during nanoparticle synthesis. Potassium persulfate is described as the initiator used in this method for enzyme-friendly nanoparticle synthesis, however, additional initiators can be substituted in the reaction such as for example but not limited to, ammonium persulfate, azo compounds (such as but not limited to, 2,2'-Azobis[2-(2-imidazolin-2-yl)propane]dihydrochloride, 2-,2'-Azobis(2-methylpropionamidine)dihydrochloride, 2,2'-Azobis[2-methyl-N-(2-hydroxyethyl)propionamide]), organic peroxides and halogen molecules, to name a few.

Experimental Procedures

1. Development of Thermally-Responsive Nanoparticles Containing Functional Organophosphorus Hydrolase Organophosphorus hydrolase (OPH, EC 3.1.8.1) (Lybradyn, Inc, Oak Brook, Ill.) hydrolyzes organophosphorus nerve agents and pesticides; it is used as a decontamination enzyme for remediation of organophosphorus nerve agents. OPH from *Geobacillus* is 37.2 kD protein that contains 8 lysine residues. The ability to stabilize OPH at elevated temperatures could be useful for many areas including but not limited to: chemical remediation, detection and decontamination. Organophosphorus hydrolase was functionalized with hydrophobic chemical groups (for example, but not limited to palmitic acid N-hydroxysuccinimide ester) and polymerizable chemical groups (for example but not limited to, acrylic acid N-hydroxysuccinimide) and encapsulated within N-isopropylacrylamide (NiPAAm)/Polystyrene particles using emulsion polymerization. Emulsion polymerization is a process known by those persons skilled in the art. N-isopropylacrylamide is a thermally-responsive polymer which undergoes a volume transition at temperatures above its lower critical solution temperature (LCST) which is approximately 32° C. At temperatures less than 32 degrees Centigrade (<32° C.), nanoparticles composed of NiPAAm are hydrophilic and highly swollen. Once heated above 32° C. the particles become more hydrophobic and shrink in size, collapsing upon themselves. Given the ability to rapidly heat the solution, the response time is nearly instantaneous.

Figure 2:
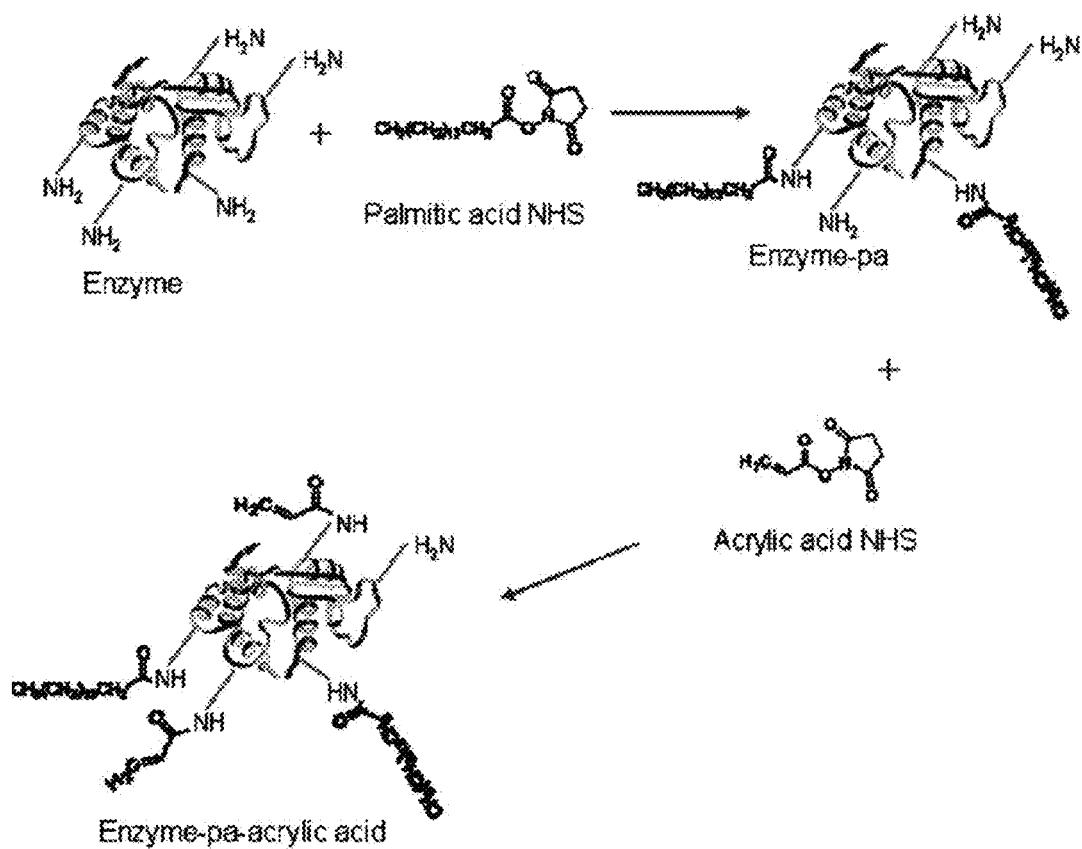
FIG. 2 shows a schematic of the 2-step enzyme modification procedure of the present invention. This modification procedure is used to increase hydrophobicity and to ensure immobilization within the nanoparticle. The enzyme is first modified with palmitic acid N-hydroxysuccinimide (paNHS) ester to create an enzyme-palmitic acid (enzyme-pa) conjugate. The enzyme-pa conjugate is further modified with acrylic acid NHS to produce a functionalized enzyme conjugate (enzyme-pa-acrylic acid), which is used as seeds in our enzyme friendly emulsion polymerization.

FIG. 2 shows the 2-step modification procedure for functionalizing OPH. Functionalization of enzymes achieves two goals: (1.) increases surface hydrophobicity which enables the enzyme to enter the interior of the aqueous micelle prior to nanoparticle synthesis, and (2.) provides a vinyl functionality that can be used to covalently anchor the enzyme 3-dimensionally within the growing polymer via free-radical polymerization. Free radical polymerization is a process known by those persons skilled in the art.

Palmitic acid N-hydroxysuccinimide (paNHS) ester (Sigma Aldrich, St. Louis, Mo.) was used to first modify OPH. Forty Four micrograms of paNHS was added for every 2 mg of OPH in an aqueous buffered system (10 mM Borate pH 8.0, 5 mM $CaCl_2$ and 150 mM NaCl). Sodium deoxycholate was also added to the reaction at 0.35% (w/v) which is above its critical micelle concentration (CMC) of 0.2%. The reaction was stirred and incubated at room temperature (approximately 23° C.) overnight. Excess paNHS and sodium deoxycholate were removed by placing the sample in a 10,000 molecular weight cut off (MWCO) Amicon centrifugation filter unit and centrifuging at 3200 rpm for 15 minutes (Fisher Scientific, Pittsburgh, Pa.).

The OPH-palmitic acid (OPH-pa) conjugate (enzyme conjugate) was then further modified with acrylic acid N-hydroxysuccinimide (aaNHS) (Sigma Aldrich, St. Louis, Mo.) in the second step of the modification procedure to produce a functionalized OPH conjugate (functionalized enzyme conjugate (seed)). Acrylic acid NHS was added to OPH-pa at a 1:1 molar ratio of aaNHS to lysine residues, in a buffer solution (10 mM Borate pH 8.0, 5 mM $CaCl_2$). The reaction was stirred at room temperature for 2 hours before removing unreacted aaNHS using centrifugation filter units that contained a 10 k MWCO membrane.

The functionalized OPH conjugates were analyzed after each modification step to determine the rate of modification. The number of grafts were assessed by a standard fluorescent assay, using fluorescamine to determine the concentration of free amines. Fluorescamine, a non-fluorescent compound, reacts with free amine groups in solution to produce a strong fluorophore at 475 nm. Extent of modification is determined by comparing fluorescence intensity of unmodified enzyme to the intensity of the functionalized enzyme. Fluorescamine reactions were performed at room temperature in a 1.5 mL cuvette using a fluorescent spectrophotometer. Fluorescamine, along with the modified enzyme sample, was added to buffered media (50 mM Borate, pH 8) and analyzed for fluorescence intensity. Enzymes were also assayed post-modification to determine the amount of remaining catalytic activity.

Figure 3:
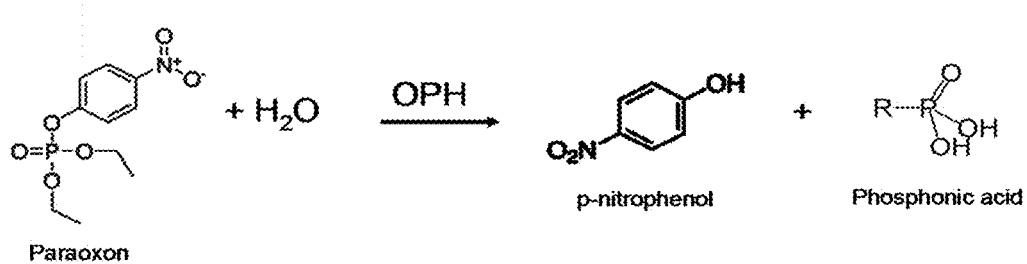
FIG. 3 shows the enzymatic assay used to determine catalytic activity of organophosphorus hydrolase (OPH). The assay is performed at room temperature by determining the increase of p-nitrophenol concentration in the presence of excess paraoxon. OPH catalyzes the hydrolysis of paraoxon; for each mole of paraoxon degraded, a mole of p-nitrolphenol and a mole of phosphonic acid are produced. The rate of the reaction is directly proportional to the production of p-nitrolphenol; the increase of p-nitrolphenol is monitored through a change in absorbance versus time.

Catalytic activity was measured throughout the modification and nanoparticle fabrication process to ensure that no step caused a significant loss in activity. FIG. 3 shows the standard assay for OPH. Organophosphorus hydrolase was assayed in a 96-well micro plate using a buffered medium (10 mM $NaPO_4$, pH 7.0) supplemented with the pesticide paraoxon (5 mM). OPH catalyzes the hydrolysis of paraoxon. OPH activity was assayed at room temperature by determining the increase of p-nitrophenol concentration in the presence of excess paraoxon. For each mole of paraoxon degraded, a mole of p-nitrophenol and a mole of phosphoric acid are produced. The rate of the reaction is directly proportional to the production of p-nitrophenol measured at 405 nm.

An enzyme-friendly fabrication procedure was developed in order to minimize the loss of catalytic activity during the synthesis reaction. At slightly above ambient temperature conditions, nanoparticles containing functionalized OPH conjugates (seeds) were prepared via standard oil-in-water emulsion polymerization protocols known by those persons skilled in the art. The seed particle (in this case the enzyme-pa-acrylic acid graft) was added to a stirred aqueous solution that contained an anionic surfactant, sodium dihexyl sulfosuccinate (MA-80). MA-80 was added drop wise to deionized water ($dH_2O$) at 3.5% (v/v) which is above its CMC of approximately 1.2% to 1.6% (v/v). Five hundred milligrams of OPH-pa-acrylic acid was added for a final concentration of 5 mg/mL OPH-pa-acrylic acid. The functionalized enzyme conjugate was added drop wise to the reactor and equilibrated for 10 minutes before the monomer mixture was added. The surfactant, MA-80 forms a micellar domain; after modification the enzyme-pa-acrylic acid conjugate is cloudy (and slightly viscous) but goes clear when added to MA-80 in water. Comonomers styrene-0.06% (w/v), and N-isopropylacrylamide (NiPAAm)-0.4%, (w/v), were added to the reaction with a cross-linker N,N'-Methylenebisacrylamide-0.053% (w/v) drop wise to the reactor and allowed to equilibrate for 10 minutes. A water soluble initiator, potassium persulfate (KPS)-0.16% (w/v) was added to initiate the polymerization. At this time, the temperature of the reaction was increased from 25° C. to 40° C. over a period of approximately 10 minutes.

Growing NiPAAm chains undergo a transition from being highly hydrophilic and swollen (at <32° C.) to shrunken and hydrophobic (at temperatures above the LCST). As the reaction temperature is raised to 40° C., the NiPAAm becomes hydrophobic and the grafting reaction occurs. Once the reaction reaches 40° C. (which takes approximately 10 minutes) the heat is removed and the stirred reactor is placed in an ice bath. A polymerization catalyst, tetramethylethylene (TEMED)-0.01% (w/v), is added to continue the free radical polymerization reaction while incubated on ice. The reaction is allowed to proceed for one hour after the addition of TEMED. After one hour, stirring is stopped and the round bottom flask is removed from the ice bath. After synthesis, samples were purified by equilibrium dialysis and centrifugation to remove unreacted monomer. After this clean up, the nanoparticles of the present invention were tested for volume response to temperature, assayed for enzymatic activity and thoroughly studied for elevated temperature stability.

Figure 4:
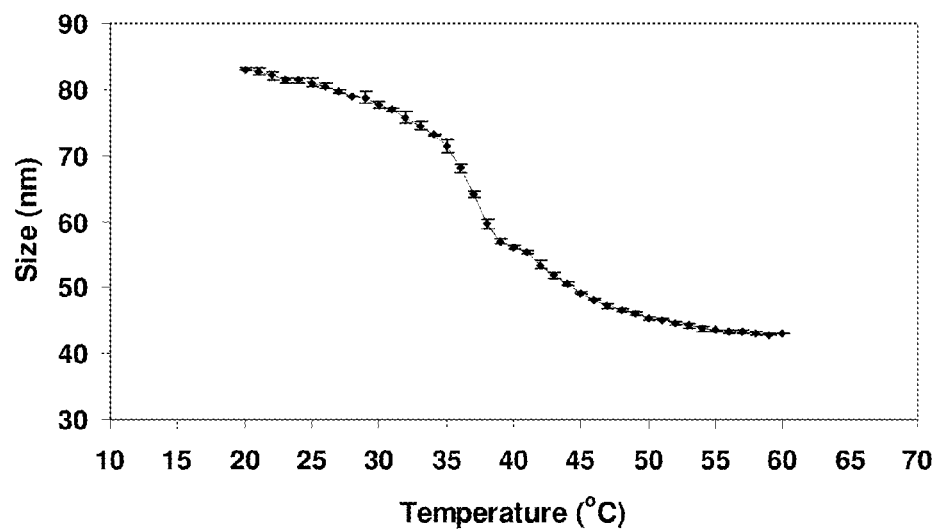
FIG. 4 shows that Dynamic light scattering (DLS) was used to determine the size distribution of particles in solution. DLS was used to measure enzyme encapsulated nanoparticle size at various temperatures from 20° C. to 60° C. Organophosphorus hydrolase (OPH) encapsulated nanoparticles size transition at various temperatures. At ambient temperatures, particles are 83 nm in size and shrink to 45 nm at elevated temperature, shrinking by 50% in size.

2. Encapsulation of Organophosphorus Hydrolase into Thermally-Responsive Nanoparticles Significantly Increases Elevated Temperature Stability Dynamic light scattering (DLS) was used to determine the size distribution of nanoparticles in solution. A Malvern Zetasizer Nano ZS was used to determine OPH encapsulated nanoparticle size at various temperatures. The nanoparticles were diluted in filtered deionized water to a final concentration of 0.25% (v/v) before nanoparticle diameter measurements were taken FIG. 4 shows the DLS size readings that were taken at one degree increments between 20° C. and 60° C. The diameter of the nanoparticles shrunk by approximately 50% when the temperature increases above NiPAAm's LCST from approximately 85 nanometers (nm) at ambient temperatures to 42 nm at elevated temperatures.

Thermal cycling was used to determine how the physical characteristics of NiPAAm respond to repeated changes in temperature from ambient to elevated temperatures. As well as how the repeated contraction and swelling of the particle affect catalytic activity of OPH encapsulated within thermally-responsive nanoparticles.

Figure 5A:
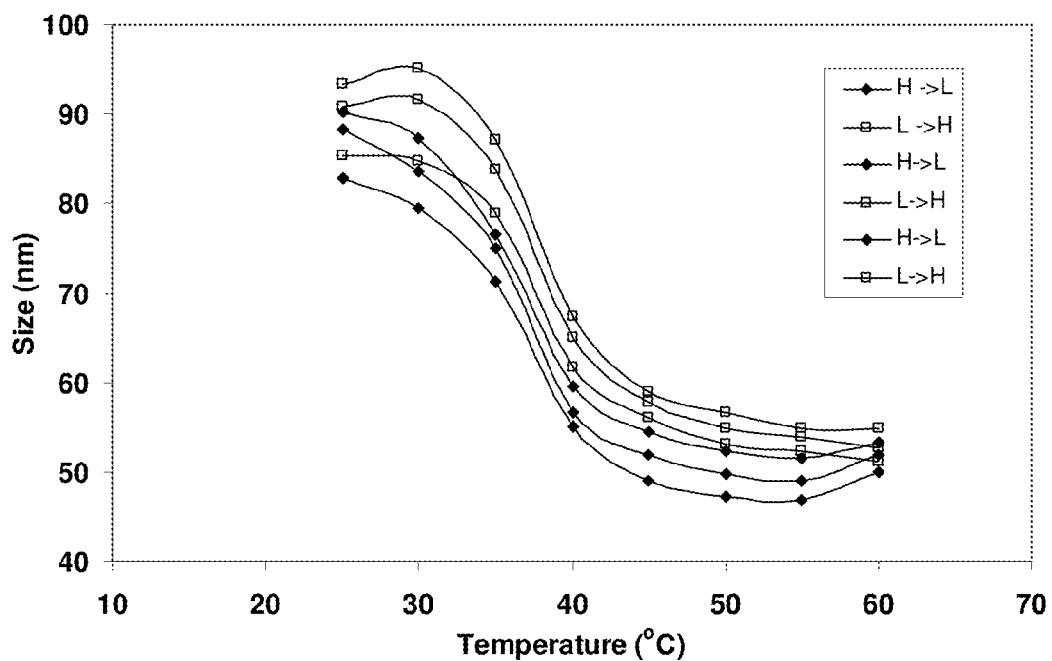
FIG. 5A shows dynamic light scattering (DLS) data on the volume transition of OPH encapsulated particles that were thermally cycled between 60° C. and 25° C. and 25° C. and 60° C. for 6 cycles. The particles continue to respond to temperature by undergoing a size change without breaking apart; nanoparticle diameter size is consistent between cycles for each temperature, indicating there is no hysteresis effect on the nanoparticles.
Figure 5B:
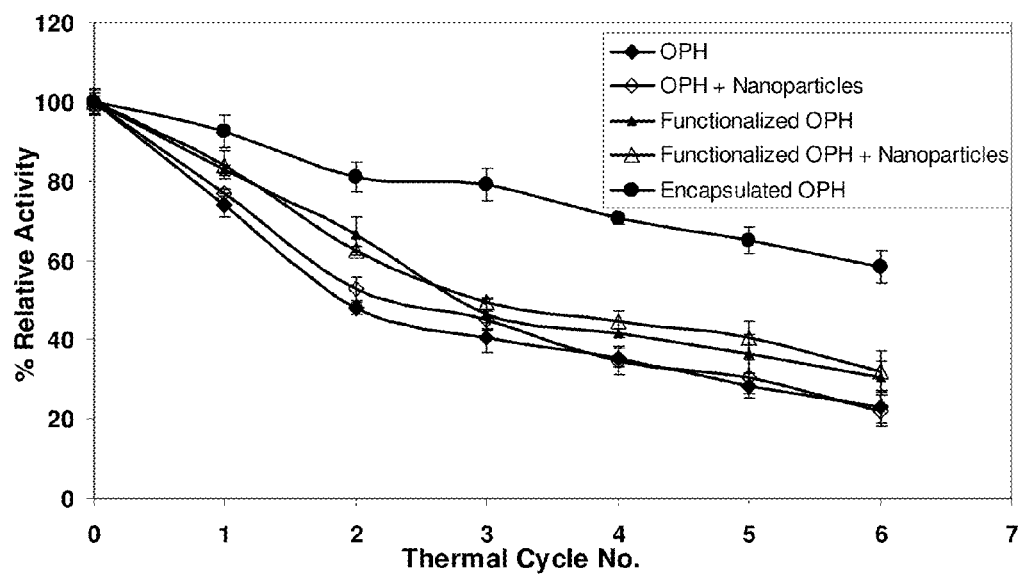
FIG. 5B shows enzymatic activity of OPH, OPH+nanoparticles, functionalized OPH, functionalized OPH+nanoparticles and OPH encapsulated nanoparticles after thermal cycling. The enzymes underwent thermal cycling from 60° C. and 25° C. and 25° C. and 60° C. for 6 cycles and activity was assayed after each cycle. Encapsulated OPH retains 60% activity after thermal stress while functionalized OPH retains less than 30% and native OPH retains only 20% activity. Encapsulation protects OPH catalytic activity during repeated thermal cycling.

Organophosphorus hydrolase encapsulated NiPAAm/Polystyrene nanoparticles were thermally cycled in the Malvern Nano ZS. Nanoparticle size was measured every 5 degrees of temperature from 25° C. to 60° C. (as shown in FIG. 5A). The starting temperature of the cycles was alternated from 60° C. to 25° C. and then 25° C. to 60° C. for 6 cycles. FIG. 5 A indicates that there is no significant hysteresis effect on the nanoparticles' size after 6 cycles. Nanoparticle diameter is consistent, at each temperature, from cycle to cycle. The nanoparticles alongside native and functionalized OPH with and without non-enzyme containing nanoparticles were incubated in an Eppendorf mastercycler gradient thermal cycler. Non-enzyme containing particles were used as a control to establish that neither the presence of thermo-responsive nanoparticle nor enzyme adsorption onto the surface of the nanoparticle were responsible for artificially increasing enzymatic stability. Non-enzyme containing nanoparticles were fabricated as previously described following a similar synthesis protocol. Thermal cycles were set to mimic the DLS thermal stress study and after each thermal cycle, aliquots from each sample were removed and assayed for enzymatic activity. FIG. 5B shows that the encapsulated OPH nanoparticles of the present invention retains 60% activity after undergoing repeated thermal stress; while native and functionalized OPH retain 20% and 30% activity, respectively. After thermal cycling between ambient and elevated temperatures, encapsulated OPH nanoparticles of the present invention retains 2-3 fold more activity than functionalized or native OPH, respectively. Further stability tests were performed to determine the effect encapsulation has on pot life, aqueous stability, at elevated temperatures.

Aqueous solutions containing native OPH, functionalized OPH, as well as nanoparticle encapsulated OPH, were incubated at various temperatures and assayed to determine their thermal half-life. Native and functionalized enzymes were added to nanoparticles, containing no enzyme, after particle synthesis to demonstrate that the adsorption of the enzyme or the presence of nanoparticles was not the cause of stability, but rather the encapsulation of the present method that increases thermal half-life. OPH samples containing 5 mg/mL enzyme and 1 mL nanoparticles or $dH_2O$ were incubated at elevated temperatures and were assayed over the course of 24 hours to determine when each enzyme would reach its half-life of thermal inactivation.

Prior to incubation at elevated temperatures the catalytic activity was assayed; half-life of thermal inactivation is established when the samples lose 50% of their original activity. FIG. 6 shows the thermal half life of inactivation in hours of OPH encapsulated nanoparticles. Through encapsulation into thermally-responsive nanoparticles of the present invention, OPH samples increase their half life 10-fold at 50° C.; a 6.67-fold increase in half-life is observed at 60° C.; and the half-life of thermal inactivation is increased 2.67 times at 70° C. In all cases, enzymes encapsulated in NiPAAm nanoparticles of the present invention retain a significantly higher degree of catalytic activity at elevated temperatures and have drastically longer half-lives. Contraction of particles at elevated temperatures increases thermal pot life (aqueous) stability.

Figure 7:
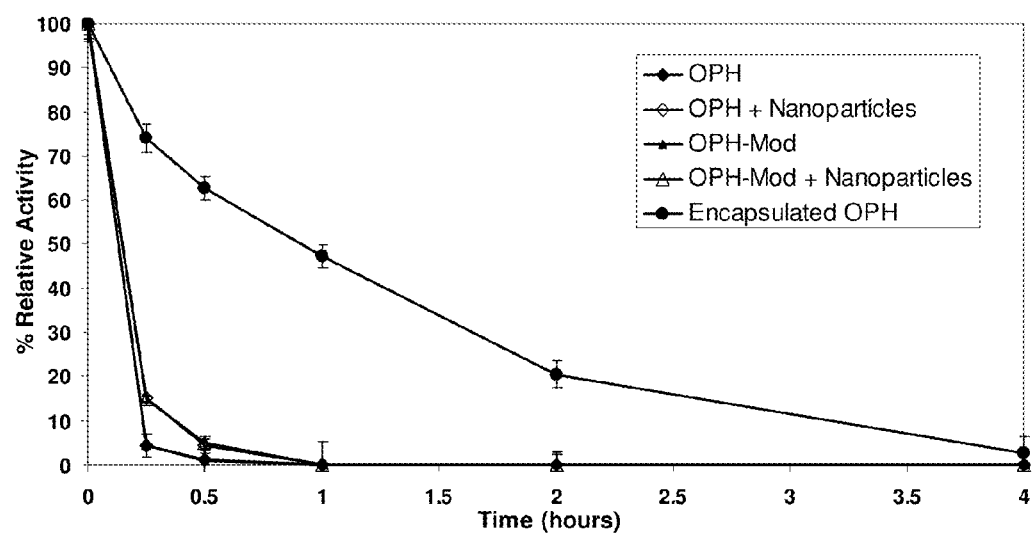
FIG. 7 shows that sodium dodecyl sulfate (SDS) is commonly used to denature enzymes for gel electrophoresis; incubating enzyme samples with SDS at 60° C. will denature all unencapsulated enzyme, proving that the encapsulated enzyme of the present invention is indeed encapsulated. Unencapsulated organophosphorus hydrolase (OPH) exhibits a complete loss of activity before 1 hour, whereas encapsulated OPH gradually loses activity over the course of 4 hours, proving OPH is encapsulated. Encapsulated OPH is more resilient, due to the steric blockage and support provided by the nanoparticle shell of the present invention

3. Verification that OPH is Encapsulated into Thermally-Responsive Nanoparticles In addition to showing prolonged stability at elevated temperatures over native, functionalized and adsorbed OPH, a method was utilized to confirm that OPH is indeed encapsulated into thermally-responsive nanoparticles. A straightforward method for probing enzyme encapsulation within NiPAAm/Polystyrene nanoparticles was established using sodium dodecyl sulfate (SDS). SDS dissociates a protein's secondary structure, unfolding the enzyme and rendering it inactive. This process is further assisted by incubating the enzyme and SDS at an elevated temperature, a common method used in gel electrophoresis for separating proteins according to their size and charge using a hydrogel. OPH and functionalized OPH (in the presence and absence of nanoparticles) alongside NiPAAm-encapsulated OPH were incubated in 2.5% (w/v) SDS at 60° C. The enzymes were periodically assayed to determine inactivation by SDS as set forth in FIG. 7. Unencapsulated enzymes, free or adsorbed, lose over 80% activity by 15 minutes and show a complete loss of activity by 1 hour. OPH that has been encapsulated within thermo-responsive particles of the present invention maintains catalytic activity up to 4 hours; the gradual loss of activity over the 4 hours may be caused by SDS diffusion into the NiPAAm/Polystyrene particles. We hypothesize that the gradual loss of activity by the OPH nanoparticles indicates that the enzyme is covalently immobilized within the interior of the particles.

Figure 8:
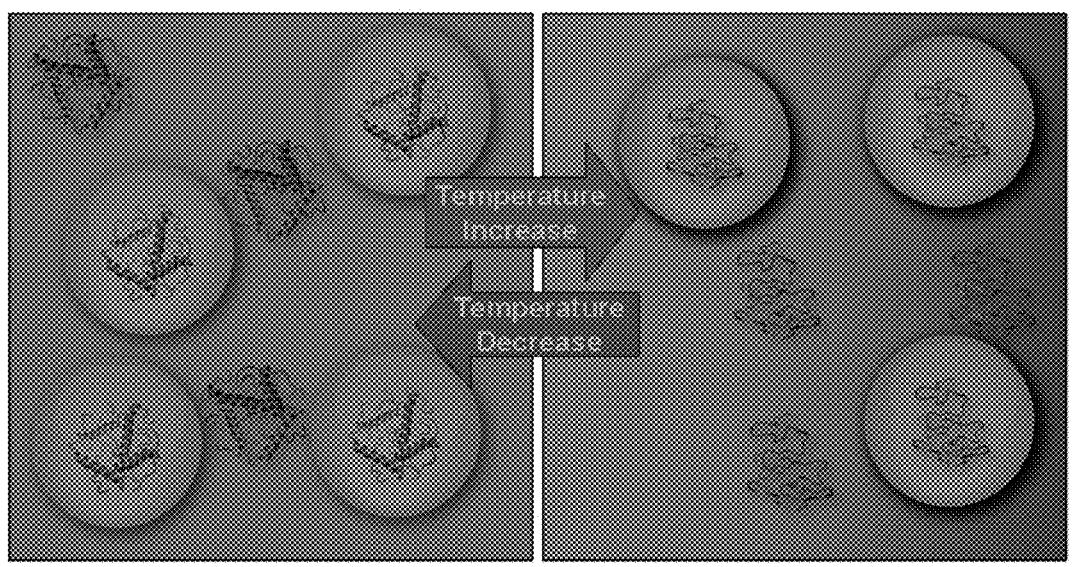
FIG. 8 shows a schematic of the affect temperatures has on free and encapsulated enzymes within non-thermally responsive polymers. Both free and non-thermally responsive encapsulated enzymes denature when exposed to increases in temperature.

4. Thermally-Induced Collapse of Temperature Responsive Particles Provide a Scaffold to Support the Enzyme and Prevent Unfolding In addition to encapsulating functionalized OPH into thermally-responsive nanoparticles, OPH was encapsulated into a non responsive nanoparticle. FIG. 8 shows both free and encapsulated enzyme within a nonthermally responsive nanoparticle at ambient and elevated temperatures. Thermally-responsive nanoparticles (as shown in FIG. 1) will collapse and protect the enzyme's tertiary structure while, a non-responsive nanoparticle only provides a moderate improvement in stability at elevated temperatures.

Non-responsive nanoparticles were created in a similar fashion to stimuli-responsive nanoparticles. At ambient conditions, nanoparticles containing functionalized OPH seeds were prepared via standard oil-in-water emulsion polymerization protocols. Oil-in-water emulsion polymerization is known by those persons skilled in the art. MA-80 was added drop wise to deionized water ($dH_2O$) at 3.5% (v/v) which is above its CMC of approximately 1.2% to 1.6% (v/v). Five hundred milligrams of OPH-pa-acrylic acid was added for a final concentration of 5 mg/mL OPH-pa-acrylic acid. Comonomers styrene-0.06% (w/v), and polyacrylamide-0.4%, (w/v), were added to the reaction with a cross-linker N,N'-Methylenebisacrylamide-0.04% (w/v) drop wise to the reactor and allowed to equilibrate for 10 minutes. An initiator, KPS-0.16% (w/v) was added to initiate the polymerization. A polymerization catalyst, TEMED-0.01% (w/v), is added to continue the free radical polymerization reaction at ambient conditions. The reaction is allowed to proceed for one hour after the addition of TEMED. After synthesis, samples were purified by equilibrium dialysis and centrifugation to remove unreacted monomer. After clean up, the thermally responsive OPH encapsulated nanoparticles (OPH/NiPAAm) of the present invention and the non-responsive OPH encapsulated nanoparticles (OPH/Acrylamide) were tested for volume response to temperature, assayed for enzymatic activity and thoroughly studied for elevated temperature stability.

Figure 9A:
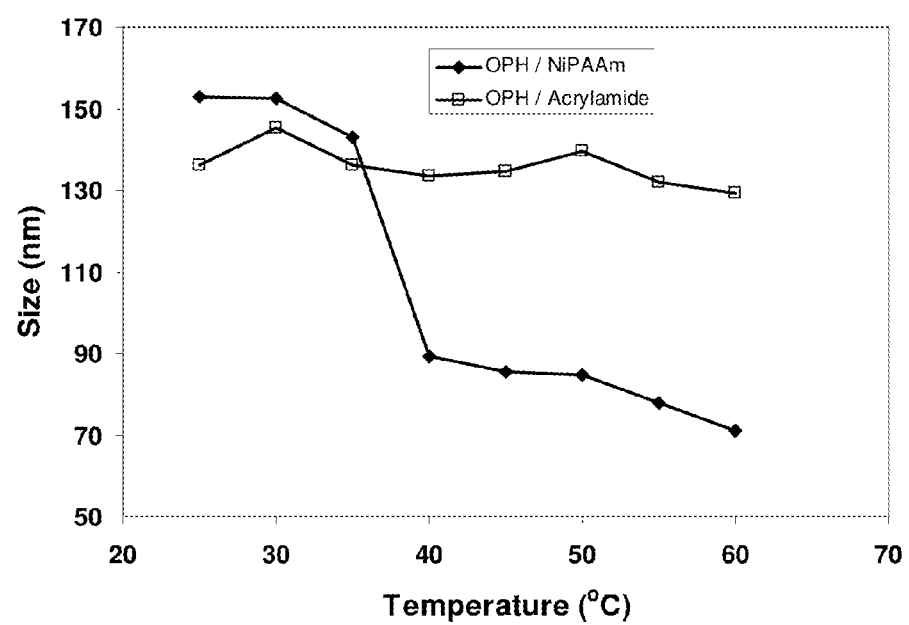
FIG. 9A shows the size change of both thermo-responsive and non stimuli responsive nanoparticles. N-isopropylacrylamide (NiPAAm), a thermo-responsive polymer, was used to create nanoparticles that shrink at elevated temperatures; on the other hand, acrylamide was used to create nanoparticles that do not respond to temperature. Unlike NiPAAm containing nanoparticles, Acrylamide nanoparticles do not respond to temperature changes.

Dynamic light scattering (DLS) was utilized to determine the size distribution and temperature responsiveness of both responsive and non-responsive OPH encapsulated nanoparticles. FIG. 9A shows the size change of both thermo-responsive and non stimuli responsive nanoparticles. N-isopropylacrylamide (NiPAAm), a thermo-responsive polymer, was used to create nanoparticles that shrink at elevated temperatures; on the other hand, acrylamide was used to create nanoparticles that do not respond to temperature. OPH/NiPAAm nanoparticle's diameters shrink at temperatures above 35° C. by approximately 50%, 150 nanometers (nm) diameter to 70 nm diameter. Whereas, OPH/Acrylamide nanoparticle's diameters do not exhibit swelling or shrinking from 25° C. to 60° C. Unlike NiPAAm nanoparticles, acrylamide nanoparticles do not respond to elevated temperatures.

Native OPH, OPH/Acrylamide and OPH/NiPAAm samples were examined for aqueous, pot life stability at elevated temperatures. The samples were incubated at 50° C., 60° C. and 70° C. and periodically assayed for OPH catalytic activity. FIG. 9B depicts the half life of thermal inactivation for OPH, OPH/Acrylamide and OPH/NiPAAm samples; The half life of thermal inactivation is noted in hours. Pot life of OPH is enhanced through encapsulation into thermo-responsive nanoparticles by 3-fold at 50° C., 2.5-fold at 60° C. and 1.6-fold at 70° C. over OPH/Acrylamide nanoparticles. The contraction of the NiPAAm nanoparticles provides steric support and prevents enzyme denaturation at elevated temperatures; catalytic activity is greatly enhanced by encapsulation within thermoresponsive nanoparticles.

Figure 10:
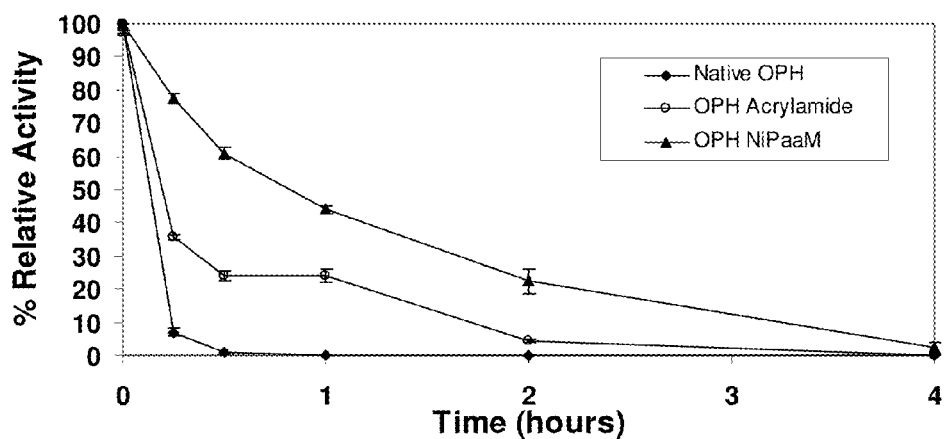
FIG. 10 shows the denaturation of enzyme by incubation with SDS. OPH, OPH/Acrylamide and OPH/NiPAAm samples were incubated at 2.5% (w/v) SDS at 60° C. for 4 hours; incubating enzyme samples with SDS at 60° C. will denature all unencapsulated enzyme and further show the enhancement of enzymatic stability when encapsulated into a thermo-responsive nanoparticle. Unencapsulated OPH loses all of its activity by 0.5 hours, OPH/Acrylamide loses almost all of its activity by 2 hours, whereas OPH/NiPAAm nanoparticle encapsulation retains activity until 4 hours.

Sodium dodecyl sulfate (SDS) was incubated with OPH, OPH/Acrylamide and OPH/NiPAAm particles at 2.5% (w/v) SDS at 60° C. for the course of 4 hours. SDS was utilized to denature the enzyme's secondary structure and further illustrate the enhancement of stability that is established when a thermo-responsive nanoparticle is utilized. As shown in FIG. 10, unencapsulated OPH loses all of its activity by 0.5 hours, OPH/Acrylamide loses all of its activity by 2 hours, whereas OPH/NiPAAm encapsulated nanoparticles of the present invention retains activity until after 4 hours of incubation with SDS at 60° C.; further supporting the enhancement of enzymatic stability when encapsulated within a thermo-responsive nanoparticle.

Figure 11:
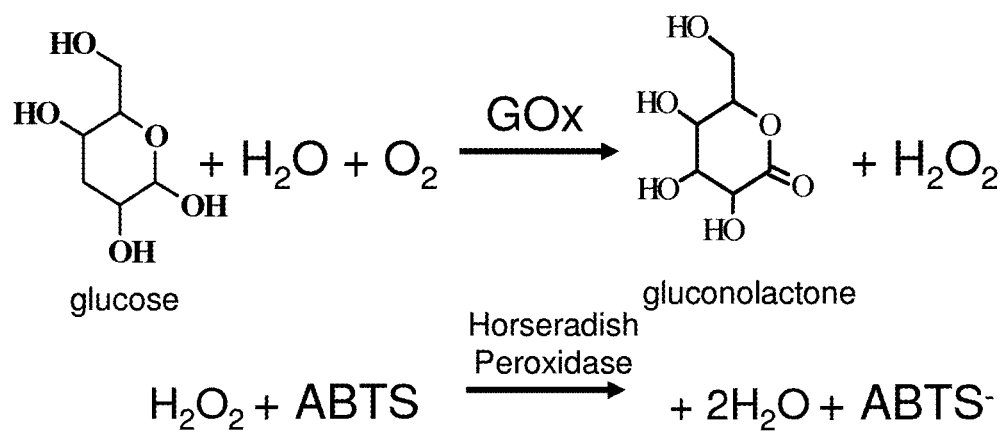
FIG. 11 shows the standard assays used to monitor catalytic activity of glucose oxidase (GOx). GOx activity is assayed at room temperature using a colorimetric assay coupled with horseradish peroxidase (HRP) in a buffered medium (100 mM $KPO_4$, pH 5). GOx converts glucose to D-Glucono-lactone and $H_2O_2$. In the presence of $H_2O_2$, HRP oxidizes 2,2'-Azino-bis(3-Ethylbenzthiazoline-6-Sulfonic Acid) (ABTS) to water and oxidized ABTS, which is measured spectrophotometrically at 405 nm.

5. Creation of Thermally-Responsive Nanoparticles Containing Functional Glucose Oxidase In addition to encapsulating a hydrolase enzyme, OPH, we have the ability to encapsulate a functional oxidase enzyme, Glucose oxidase (GOx, EC 1.1.3.4) (Sigma Aldrich, St. Louis, Mo.) which converts glucose into D-gluconic acid and peroxide (as shown in FIG. 11). The reaction is coupled with peroxidase which, in conjunction with an oxidoreductase dye, converts peroxide and dye into a colored product. GOx from *Aspergillus niger* is a dimer consisting of two 80 kD subunits and 30 lysines. GOx was functionalized with hydrophobic chemical groups (for example, but not limited to, palmitic acid N-hydroxysuccinimide ester) and polymerizable chemical groups (such as for example but not limited to, acrylic acid N-hydroxysuccinimide), as shown in FIG. 2 and the functionalized enzyme conjugates used as seeds for encapsulation within N-isopropylacrylamide (NiPAAm)/Polystyrene particles using emulsion polymerization. Emulsion polymerization is a process known by those persons skilled in the art. The ability to stabilize GOx and other oxidase enzymes is useful for many industries such as but not limited: drug delivery and wound healing.

Functionalized GOx was analyzed after modification with palmitic acid N-hydroxysuccinimide ester (paNHS) and acrylic acid N-hydroxysuccinimide (aaNHS) to determine the degree of modification that occurred. The rate of modification was determined by utilizing a fluorescent assay that detects the number of free amines. Fluorescamine, a non-fluorescent compound, reacts with free amine groups in solution to produce a fluorophore at 475 nm. The rate of modification is determined by comparing the intensity of native GOx to functionalized GOx.

Catalytic activity of GOx was measured after each modification step and throughout the nanoparticle fabrication process to ensure that no step caused a considerable loss in activity. Glucose oxidase activity is assayed at room temperature using a colorimetric assay coupled with horseradish peroxidase (HRP) in a buffered medium (100 mM $KPO_4$, pH 5). GOx converts glucose to D-Glucono-lactone and $H_2O_2$ In the presence of $H_2O_2$, HRP oxidizes 2,2'-Azino-bis(3-Ethylbenzthiazoline-6-Sulfonic Acid)(ABTS) to water and oxidized ABTS, which is measured spectrophotometrically at 405 nm.

Thermally-responsive (thermoresponsive) nanoparticles were created using functionalized GOx as seeds, the functionalization allows the GOx to be used a co-monomer during the fabrication process via standard oil-in-water emulsion polymerization protocols. The seed particle (GOx-pa-acrylic acid) was added to a stirred aqueous solution, under nitrogen, that contained an anionic surfactant, MA-80. MA-80 was added drop wise at 3.5% (v/v). The concentration of enzyme added to the reactor was dependant upon the amount required for activity assays. Fifty milligrams of GOx-pa-acrylic acid was added to the 100 mL round bottom reactor, for a final concentration of 0.5 mg/mL GOx-pa-acrylic acid. The functionalized enzyme was added drop wise to the reactor and equilibrated for 10 minutes. Comonomers styrene-0.06% (w/v), and NiPAAm-0.4%, (w/v), were added to the reaction with a cross-linker N,N'-Methylenebisacrylamide-0.053% (w/v) drop wise to the reactor and allowed to equilibrate for 10 minutes. A water soluble initiator, KPS-0.16% (w/v) was added to initiate the polymerization. At this time, the temperature of the reaction was increased from 25° C. to 40° C. over a period of approximately 10 minutes. Once the reaction reached 40° C. the heat was removed and the stirred reactor was placed in an ice bath. A polymerization catalyst, TEMED-0.01% (w/v), was added to continue the free radical polymerization reaction while incubated on ice. The reaction was allowed to proceed for one hour after the addition of TEMED. After one hour, stirring is stopped and the round bottom flask is removed from the ice bath. After synthesis, samples were purified by equilibrium dialysis and centrifugation to remove unreacted monomer. After clean up, the nanoparticles were tested for volume response to temperature, assayed for enzymatic activity, and thoroughly studied for elevated temperature stability in both the aqueous state (pot life) and dry state (shelf life).

Figure 12:
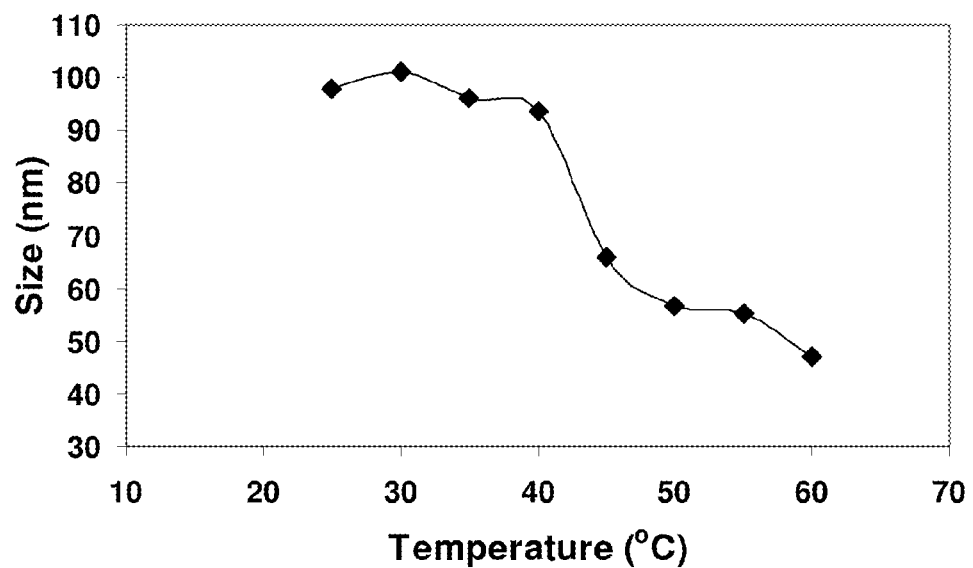
FIG. 12 shows that Dynamic light scattering (DLS) was used to determine the size distribution of GOx encapsulated nanoparticles in solution. The temperature of the DLS was varied from 25° C. to 60° C. and the size and distribution of the particles were measured every 5 degrees. GOx encapsulated nanoparticles are 95 nm at ambient temperatures and shrink by approximately 50% at elevated temperatures to 50 nm.

6. Thermally-Induced Volume Transition of Nanoparticles Protects Glucose Oxidase Catalytic Activity from Elevated Temperatures Increasing Both Pot Life and Shelf Life Stability Dynamic light scattering (DLS) was used to determine the diameter size and particle distribution of GOx encapsulated nanoparticles in solution. The nanoparticles were diluted in filtered deionized water to a final concentration of 0.25% (v/v) before measurements were taken. FIG. 12 depicts the DLS size readings that were taken at 5 degree increments for GOx encapsulated nanoparticles from 25° C. to 60° C. In their swollen state, the particles were approximately 95 nanometers (nm) and as temperature increased the particles shrunk by 50% to less than 50 nm in diameter. The size transition occurs at slightly above 40° C., which is above NiPAAm's LCST. After determining the particles were thermally responsive, the aqueous stability or pot life was thoroughly examined.

Aqueous solutions containing native GOx, native GOx with non-enzyme containing nanoparticles, functionalized GOx, functionalized GOx with non-enzyme containing nanoparticles, as well as nanoencapsulated GOx were incubated at various temperatures and assayed to determine their thermal half-life. Non-enzyme containing nanoparticles were fabricated as previously described and utilized to ensure the presence of nanoparticles or the adsorption of enzyme to the nanoparticle surface would artificially increase GOx catalytic stability at elevated temperatures.

Before incubation at elevated temperatures, GOx samples were assayed; half life of thermal inactivation occurs when the GOx samples lose 50% of their original activity. GOx samples containing 0.5 mg/mL enzyme and 1 mL nanoparticles or $dH_2O$ were incubated at 50° C., 60° C. and 70° C. and were assayed throughout 48 hours. FIG. 13 depicts the half life of GOx samples, in hours, at elevated temperatures. Through encapsulation into thermally-responsive nanoparticles, GOx's half life is increased at 50° C. by 8 times over unencapsulated controls; a 15-fold increase occurred at 60° C. and at least a 2-fold increase in thermal half-life occurs when incubated at 70° C. The pot life, aqueous stability, of GOx is significantly increased through encapsulation into thermally responsive nanoparticles over native or functionalized GOx.

Figure 14:
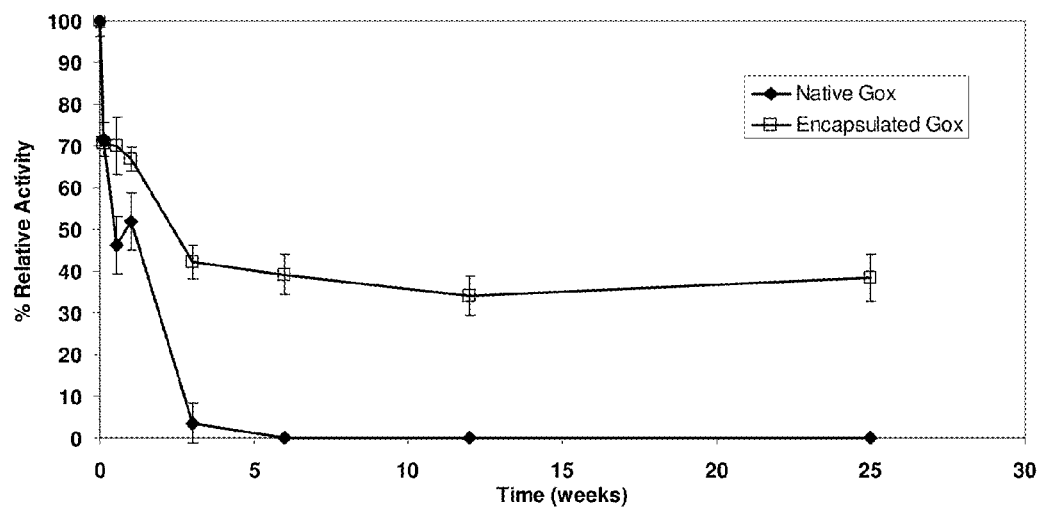
FIG. 14 shows the dry storage stability (shelf life) of glucose oxidase (GOx) and encapsulated GOx was lyophilized and stored continuously as a dry powder at 70° C. Native GOx loses all activity after 3 weeks of storage, while encapsulated GOx retains approximately 40% activity after 6 months at 70° C. Shelf life of GOx at elevated temperatures is greatly enhanced by encapsulation into thermoresponsive nanoparticles

Shelf life stability or dry storage stability of GOx was also investigated as shown in FIG. 14. Dry storage stability at 70° C. was studied to determine how encapsulation of enzymes within thermo-responsive nanoparticles extends shelf-life. Lyophilization, or freeze drying, is often used to extend the shelf life of enzymes while maintaining biological activity. The addition of excipients enables the enzyme to retain its active tertiary folding structure as the water is removed during lyophilization. Trehalose was used because it is a known natural lyoprotectant, a molecule similar to a cryoprotectant that helps protect freeze dried material. Trehalose is produced by a variety of plant, fungi and invertebrate animals that remain in a state of suspended animation during periods of drought, and is known to enhance thermal stability of lyophilized GOx. Glucose oxidase encapsulated nanoparticles alongside native GOx were lyophilized with and without various amounts of stabilizer to determine the best ratio of stabilize to enzyme mass ratio. GOx and encapsulated GOx were lyophilized and studied in the presence of a 50:1 mass ratio of trehalose to enzyme. After lyophilization the enzymes were assayed for catalytic activity and stored dry as powdered aliquots continuously at 70° C. Lyophilization of these materials extends their shelf life over that of native enzyme. FIG. 10 shows that native enzyme lost all activity after 3 weeks of storage at 70° C.; whereas encapsulated functionalized enzyme conjugates of the present invention remained catalytically active after storage at 70° C. for over 6 months, retaining approximately 40% activity. There is an initial decrease in encapsulated GOx activity, however this decrease stabilizes and the enzyme's activity remains around 40%. Lyophilization of encapsulated enzymes further extends dry shelf life stability at elevated temperatures from 3 weeks to over 6 months. Shelf life of GOx at elevated temperatures is greatly enhanced by encapsulation into thermoresponsive nanoparticles of the present invention 7. Creation of Acetylcholinesterase Encapsulated Thermally-Responsive Nanoparticles In addition to providing methods of the present invention for encapsulation of a functionally active and 3-dimensionally immobilized, organophosphorous hydrolase (a hydrolase enzyme), an oxidase enzyme, and a glucose oxidase, the present invention further provides a method for encapsulating acetylcholinesterase (AChE) into thermally-responsive nanoparticles. Acetylcholinesterase (EC 3.1.1.7) (Sigma Aldrich, St. Louis, Mo.), an enzyme of the central nervous system, is inhibited by V-series nerve agents; thus the inhibition of AChE can be utilized for detection of nerve agents. The ability to stabilize AChE at elevated temperatures is useful for many areas including: for example chemical detection and remediation as well as in the field of drug delivery.

Acetylcholinesterase was functionalized with at least one hydrophobic chemical group (such as for example, palmitic acid N-hydroxysuccinimide ester) and at least one polymerizable chemical group (such as for example, acrylic acid N-hydroxysuccinimide) in a 2-step modification procedure (as set forth in FIG. 2) which increases surface hydrophobicity enabling the enzyme to enter the interior of the aqueous micelle prior to nanoparticle synthesis, and provides a vinyl functionality that can be used to covalently anchor the enzyme 3-dimensionally within the growing polymer via free-radical polymerization. The degree of functionalization is monitored after each modification step by comparing the fluorescent intensity of native and modified enzyme using a standard fluorescent assay, fluorescamine. Catalytic activity of AChE is also monitored throughout the modification and nanoparticle fabrication procedure.

Figure 15:
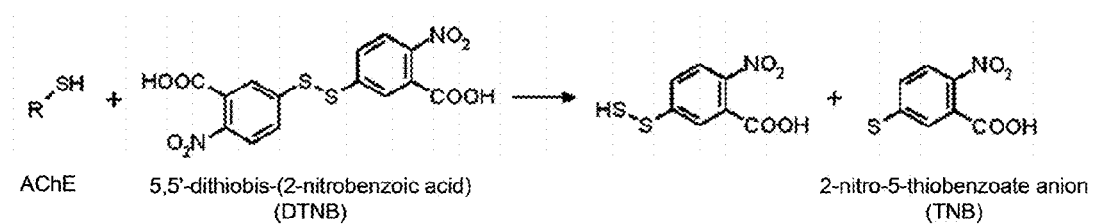
FIG. 15 shows the enzymatic assay used to monitor catalytic activity of acetylcholinesterase (AChE). The assay used Ellman's reagent (5,5'-dithiobis-(2-nitrobenzoic acid, otherwise known as "DTNB") that is a chemical used to quantify the number or concentration of thiol groups in a sample. The assay uses the thiol ester acetylthiocholine instead of the oxy ester acetylcholine. AChE hydrolyses the acetylthiocholine to produce thiocholine and acetate. The thiocholine in turn reduces the DTNB, which absorbs at 405 nm.
Figure 17A:
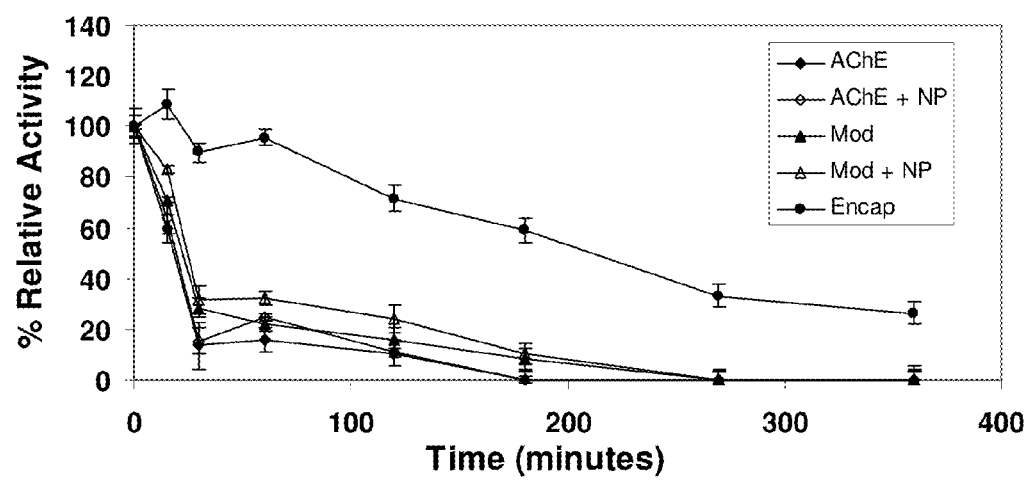
FIGS. 17A-B show acetylcholinesterase (AChE) containing samples' aqueous stability (pot life) at elevated temperatures of 40 degrees Centigrade and 50 degrees Centigrade, respectively, for the following samples: acetylcholinesterase ("AChE"), AChE+nanoparticles ("AChE+NP"), functionalized AChE conjugate ("Mod"), functionalized AChE conjugate+nanoparticles ("Mod+NP"), and functionalized AChE conjugate encapsulated thermally responsive nanoparticles of the present invention ("Encap").
Figure 17B:
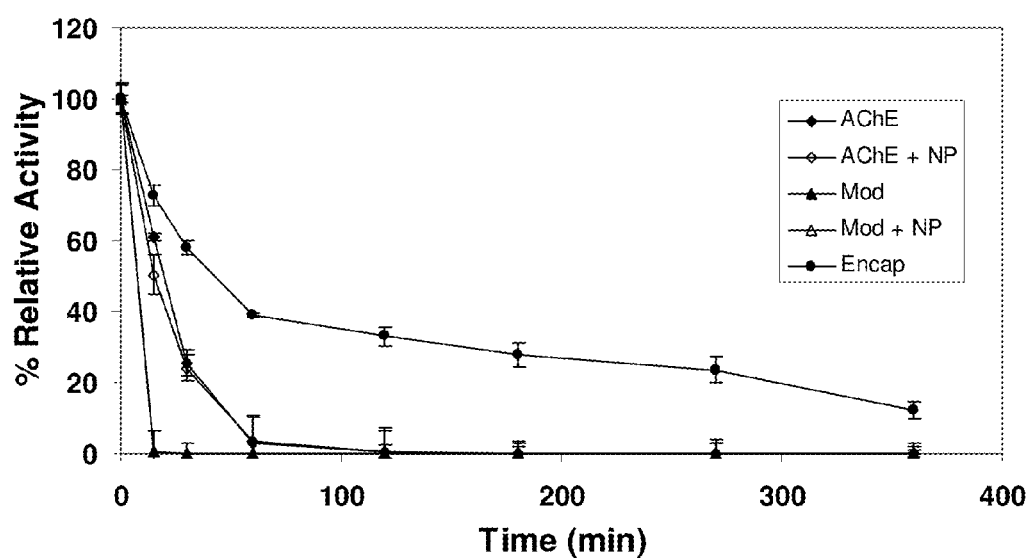

Catalytic activity of AChE is measured by utilizing 5'-dithiobis-(2-nitrobenzoic acid or DTNB. DTNB is a chemical used to quantify the number or concentration of thiol groups in a sample. FIG. 15 shows the AChE assay which uses the thiol ester acetylthiocholine instead of the oxy ester acetylcholine. AChE hydrolyses the acetylthiocholine to produce thiocholine and acetate. The thiocholine in turn reduces the DTNB, which absorbs at 405 nm.

The AChE-pa-acrylic acid conjugate (seed) that resulted from the inventions two step modification as set forth herein, was further used in an enzyme-friendly nanoparticle fabrication method of the present invention. This enzyme-friendly fabrication method minimizes the loss of catalytic activity during the synthesis reaction. Surfactant was eliminated from this nanoparticle method in order to maintain AChE catalytic activity during the fabrication process. At slightly above ambient conditions, nanoparticles containing functionalized AChE seeds were created. Four milligrams of AChE-pa-acrylic acid conjugate was added drop wise to a stirred aqueous solution under nitrogen for a final concentration of 0.04 mg/mL AChE-pa-acrylic acid conjugate and allowed to equilibrate for 10 minutes. Comonomers styrene-0.06% (w/v), and NiPAAm-0.4%, (w/v), were added to the reaction with a cross-linker N,N'-Methylenebisacrylamide-0.053% (w/v) drop wise to the reactor and allowed to equilibrate for 10 minutes. An initiator, KPS-0.16% (w/v) was added to initiate the polymerization. At this time, the temperature of the reaction was increased from 25° C. to 40° C. over a period of approximately 10 minutes. After the reaction reaches 40° C. (which takes approximately 10 minutes) the heat is removed and the stirred reactor is placed in an ice bath. A polymerization catalyst, TEMED-0.01% (w/v), is added to continue the free radical polymerization reaction while incubated on ice. The reaction is allowed to proceed for one hour after the addition of TEMED. After one hour, stirring is stopped and the round bottom flask is removed from the ice bath. After synthesis, samples were purified by equilibrium dialysis and centrifugation to remove unreacted monomer. After clean up, the nanoparticles of the present invention were tested for volume response to temperature, assayed for enzymatic activity and thoroughly studied for elevated temperature stability.

8. Encapsulation of Acetylcholinesterase into Thermally-Responsive Nanoparticles Increases Elevated Temperature Stability Acetylcholinesterase (AChE) encapsulated into thermally responsive nanoparticles of the present invention were analyzed via DLS to determine their diameter size, particle distribution and volume transition due to temperature changes. FIG. 16 shows AChE encapsulated nanoparticles and their size response to temperature. AChE encapsulated into thermally-responsive nanoparticles were diluted to 0.5% (v/v) and analyzed via DLS at one degree increments from 20° C. to 60° C. At ambient temperatures, the particles are approximately 320 nanometers (nm) and shrink to 225 nm at elevated temperatures. The diameter size of the AChE encapsulated particles are larger than those particles made by methods that contain surfactant in the fabrication process. After determining the particles were thermally responsive, the aqueous stability or pot life was examined.

Aqueous solutions containing native AChE, native AChE incubated with non-enzyme containing thermally-responsive nanoparticles, functionalized AChE, functionalized AChE incubated with non-enzyme containing thermally-responsive nanoparticles, and AChE encapsulated into thermally-responsive nanoparticles of the present invention were incubated at 40° C. and 50° C. to determine their aqueous thermal half life of inactivation. Non-enzyme containing thermally-responsive nanoparticles were fabricated in the exact manner. AChE encapsulated nanoparticles were created but without enzyme and used to ensure that the presence of nanoparticles or enzyme adsorption onto nanoparticles artificially stabilize AChE activity at elevated temperatures.

Before incubation at elevated temperatures, AChE samples were assayed; half life of thermal inactivation occurs when the AChE samples lose 50% of their original activity. AChE samples containing 0.04 mg/mL enzyme and 1 mL nanoparticles or $dH_2O$ were incubated at 40° C. and 50° C. and were assayed over the course of 6 hours. FIG. 17A depicts the activity of the AChE samples at 40° C. throughout the time course. Through encapsulation into thermally-responsive nanoparticles, AChE half life is increased at 40° C. by 6 times over unencapsulated controls. FIG. 17B shows the activity of AChE samples at 50° C. over the course of 6 hours. Encapsulation into thermally-responsive nanoparticles increases AChE half-life of inactivation at 50° C. by 3.5 times over unencapsulated enzyme. The pot life, aqueous stability, of AChE is increased through encapsulation into thermally responsive nanoparticles over native or functionalized AChE.

9. Creation of Thermally-Responsive Nanoparticles Containing Functional Proteins A protein is functionalized with hydrophobic and polymerizable chemical groups as defined and described hereinabove in the two step modification process of the present invention. The resulting functionalized protein conjugate is then utilized as a seed for thermally-responsive nanoparticle synthesis. The protein-friendly fabrication procedure of the present invention minimizes the loss of protein during the synthesis reaction. At ambient, slightly above ambient, or below ambient conditions, nanoparticles containing functionalized protein conjugates (seeds) were prepared. The functionalized protein conjugate (seed) is added to a stirred reactor that contained deionized water that had been bubbled with nitrogen. The functionalized protein conjugate is added drop wise to the reactor and is equilibrated for 10 minutes before a thermally responsive monomer, as defined and described hereinabove, is added. The monomer, when polymerized, becomes thermo-responsive is then added dropwise to the reactor and equilibrated for 10 minutes. A crosslinker, as defined and described hereinabove, may or may not be added to the reactor during monomer addition. Following equilibration, an initiator, as defined and described hereinabove, may or may not be added dropwise to the reactor. The nanoparticle fabrication procedure of the present invention is allowed to proceed until monodisperse nanoparticles of the present invention are formed.

Although the invention has been described in detail in the foregoing for the purpose of illustration, it was to be understood that such detail is solely for that purpose and that variations can be made therein by those skilled in the art without departing from the spirit and scope of the invention except as it may be limited by the claims.

What is claimed is:

1. A method for protecting nanocatalysts comprising one or more proteins from environmental conditions, said method comprising:

immobilizing one or more nanocatalysts comprising the proteins and completely encapsulating said one or more immobilized nanocatalysts comprising the proteins within one or more thermally responsive polymeric nanoparticles by raising the temperature above the lower critical solution temperature of said thermally responsive polymeric nanoparticles during an initiation process wherein said nanoparticles undergo a conformational change when heated whereby protecting said nanocatalysts comprising the proteins from temperatures greater than 30 degrees Centigrade.

2. The method of claim 1, wherein said one or more proteins is/are at least one enzyme or biological catalyst.

3. The method of claim 2 further including grafting at least one moiety to a surface of said at least one enzyme to bind to said polymeric nanoparticles for forming modified enzymes.

4. The method of claim 3, wherein said at least one moiety is a vinyl group.

5. The method of claim 3 further including subjecting said modified enzymes to a polymerization process.

6. The method of claim 5 further including employing a free-radical addition polymerization process or a living radical polymerization process.

7. The method of claim 6, wherein said free-radical addition polymerization process is selected from the group consisting of an emulsion polymerization process and a non-emulsion polymerization process.

8. The method of claim 7, wherein said free-radical addition polymerization process optionally includes at least one thermally responsive comonomer selected from the group consisting of N-isopropylacrylamide, poly (isopropyl-N-vinylpyrolidone), and combinations thereof.

* * * * *